US011572409B2

(12) United States Patent
Olive et al.

(10) Patent No.: US 11,572,409 B2
(45) Date of Patent: Feb. 7, 2023

(54) ANTIBODIES HAVING SPECIFICITY FOR BTN2 AND USES THEREOF

(71) Applicants: IMCHECK THERAPEUTICS SAS, Marseilles (FR); INSERM (INSTITUT NATIONAL DE LA SANTÉ ET DE LA RECHERCHE MÉDICALE), Paris (FR); INSTITUT JEAN PAOLI & IRENE CALMETTES, Marseilles (FR); UNIVERSITÉ D'AIX-MARSEILLE, Marseilles (FR); CENTRE NATIONAL DE LA RECHERCHE SCIENTIFIQUE—CNRS, Paris (FR)

(72) Inventors: Daniel Olive, Marseilles (FR); Christine Pasero, Marseilles (FR)

(73) Assignees: IMCHECK THERAPEUTICS SAS, Marseilles (FR); INSERM, Paris (FR); INSTITUT JEAN PAOLI & IRENE CALMETTES, Marseilles (FR); UNIVERSITÉ D'AIX-MARSEILLE, Marseilles (FR); CNRS, Paris (FR)

( * ) Notice: Subject to any disclaimer, the term of this patent is extended or adjusted under 35 U.S.C. 154(b) by 201 days.

(21) Appl. No.: 16/648,886

(22) PCT Filed: Sep. 21, 2018

(86) PCT No.: PCT/EP2018/075689
§ 371 (c)(1),
(2) Date: Mar. 19, 2020

(87) PCT Pub. No.: WO2019/057933
PCT Pub. Date: Mar. 28, 2019

(65) Prior Publication Data
US 2020/0283519 A1 Sep. 10, 2020

(30) Foreign Application Priority Data

Sep. 21, 2017 (EP) .................................... 17306238
Nov. 10, 2017 (EP) .................................... 17306563

(51) Int. Cl.
*C07K 16/28* (2006.01)
(52) U.S. Cl.
CPC ...... *C07K 16/2803* (2013.01); *C07K 2317/21* (2013.01); *C07K 2317/24* (2013.01); *C07K 2317/92* (2013.01)
(58) Field of Classification Search
CPC ........................ C07K 16/2803; C07K 2317/92
USPC ...................................................... 424/172.1
See application file for complete search history.

(56) References Cited

U.S. PATENT DOCUMENTS

| | | | | |
|---|---|---|---|---|
| 9,334,331 B2 * | 5/2016 | Igawa | ..................... | C07K 16/40 |
| 10,421,807 B2 * | 9/2019 | Gonzales | ................ | A61P 17/08 |
| 2014/0242077 A1 * | 8/2014 | Choi | .................. | C07K 16/2809 |
| | | | | 424/136.1 |

FOREIGN PATENT DOCUMENTS

| | | |
|---|---|---|
| WO | 2009/030884 A2 | 3/2009 |
| WO | 2012/080351 A1 | 6/2012 |
| WO | 2015/077544 A1 | 5/2015 |

OTHER PUBLICATIONS

Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
George et al. (Circulation. 1998; 97: 900-906).*
Almagro & Franssen, Frontiers in Bioscience, 13:1619-33 (2008).*
Marchalonis et al., Dev & Comp Immunol. 30:223-247 (2006).*
Lippow et al., "Computational design of antibody-affinity improvement beyond in vivo maturation," Nature Biotechnology, 25(10): 1171-1176 (2007).*
Sulea et al., "Application of Assisted Design of Antibody and Protein Therapeutics (ADAPT) improves efficacy of a Clostridium difficile toxin A single-domain antibody," Scientific Reports, 8(260):1-11 (2018).*
Hasegawa et al., "Single amino acid substitution in LC-CDR1 induces Russell body phenotype that attenuates cellular protein synthesis through elF2a phosphorylation and thereby downregulates IgG secretion despite operational secretory pathway traffic," MABS, vol. 9, No. 5, pp. 854-873 (2017).*
Altshuler et al., "Generation of Recombinant Antibodies and Means for Increasing Their Affinity," Biochemistry (Moscow), 75(13): 1584-1605 (2010).*
Vajda et al., "Progress toward improved understanding of antibody maturation," Current Opinion in Structural Biology, 67 pp. 226-231 (2021).*
Marks et al., "How repertoire data are changing antibody science," J. Biol. Chem. 295(29) 9823-9837 (2020).*
Akbar et al., Cell Reports 34, 108856, Mar. 16, 2021).*
Lo et al., "Conformational epitope matching and prediction based on protein surface spiral features," BMC Genomics vol. 22, Article No. 116 (2021).*
Palakodeti et al.; "The Molecular Basis for Modulation of Human V[gamma]9V[delta]2 T Cell Responses by CD277/Butyrophilin-3 (BTN3A)-specific Antibodies"; Journal of Biological Chemistry, vol. 287, No. 39, Sep. 21, 2012, pp. 32780-32790.

(Continued)

*Primary Examiner* — Lynn A Bristol
(74) *Attorney, Agent, or Firm* — WCF IP

(57) ABSTRACT

The present invention relates to antibodies having specificity for BTN2 and uses thereof, in particular for the treatment of cancer.

6 Claims, 5 Drawing Sheets

Figure 1:
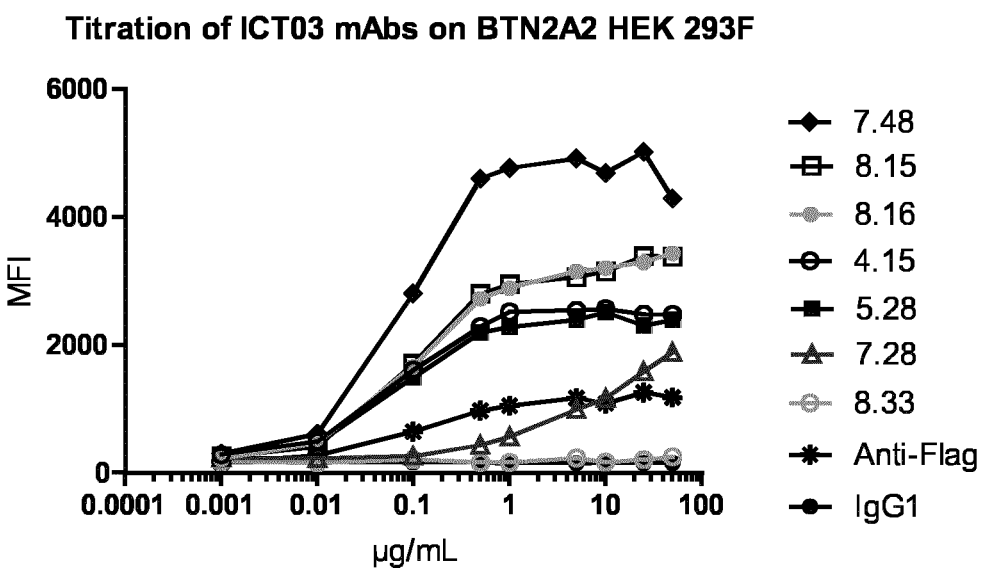
Figure 1:
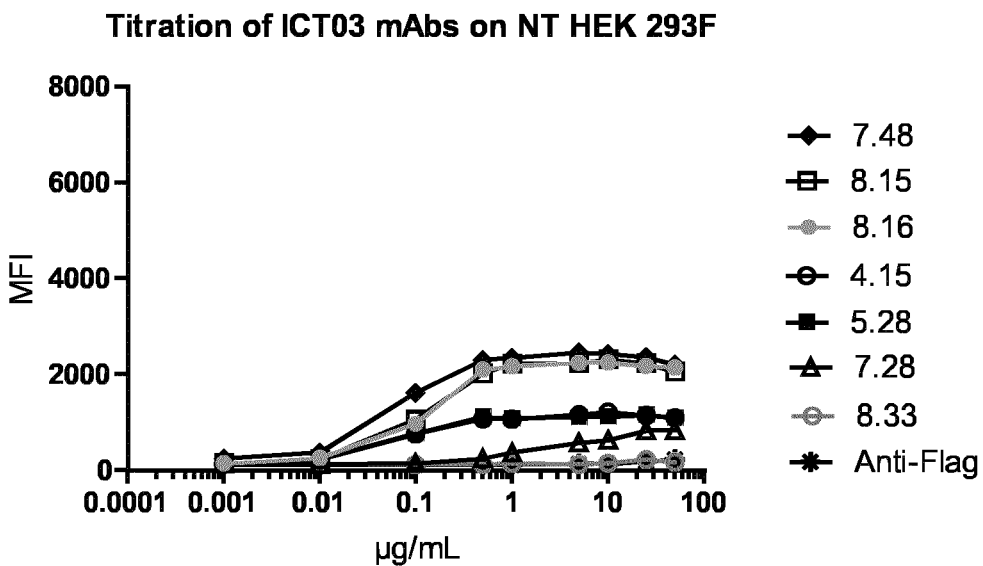

Specification includes a Sequence Listing.

(56) References Cited

OTHER PUBLICATIONS

Arnett et al.; "Immune modulation of butyrophilins"; The Journal of Immunology, vol. 14, No. 8, Jul. 25, 2014, pp. 559-569.

Smith et al.; "BTN1A1, the Mammary Gland Butyrophilin, and BTN2A2 Are Both Inhibitors of T Cell Activation"; Journal of Immunology, vol. 184, No. 7, Apr. 2010, pp. 3514-3525.

Ammann et al.; "Butyrophilin Btn2a2 Inhibits TCR Activation and Phosphatidylinositol 3-Kinase/Akt Pathway Signaling and Induces Foxp3 Expression in T Lymphocytes"; The Journal of Immunology, vol. 190, No. 10, May 15, 2013, pp. 5030-5036.

Guo et al.; "Novel Immune Check-Point Regulators in Tolerance Maintenance"; Frontiers in Immunology, vol. 6, Aug. 18, 2015, entire article.

Arnett et al.; "Immune modulation of butyrophilins"; Nature Reviews Immunology, vol. 14, No. 8, pp. 559-569, Jul. 25, 2014.

EP3684795, Third Party Observation, Nov. 16, 2020.

WO2020/188086, PCT/EP2020/057794, Internatioal Searching Authority.

Rigau et al: "Butyrophilin 2A1 is essential for phosphoantigen reactivity by [gamma delta] T cells", Science, Jan. 9, 2020.

\* cited by examiner

A

B

A

B

SEQUENCE LISTING

<160> NUMBER OF SEQ ID NOS: 114

<210> SEQ ID NO 1
<211> LENGTH: 527
<212> TYPE: PRT
<213> ORGANISM: Homo sapiens

<400> SEQUENCE: 1

```
Met Glu Ser Ala Ala Ala Leu His Phe Ser Arg Pro Ala Ser Leu Leu
1               5                   10                  15

Leu Leu Leu Leu Ser Leu Cys Ala Leu Val Ser Ala Gln Phe Ile Val
            20                  25                  30

Val Gly Pro Thr Asp Pro Ile Leu Ala Thr Val Gly Glu Asn Thr Thr
        35                  40                  45

Leu Arg Cys His Leu Ser Pro Glu Lys Asn Ala Glu Asp Met Glu Val
    50                  55                  60
```

-continued

```
Arg Trp Phe Arg Ser Gln Phe Ser Pro Ala Val Phe Val Tyr Lys Gly
 65                  70                  75                  80

Gly Arg Glu Arg Thr Glu Gln Met Glu Glu Tyr Arg Gly Arg Thr
                 85                  90                  95

Thr Phe Val Ser Lys Asp Ile Ser Arg Gly Ser Val Ala Leu Val Ile
                100                 105                 110

His Asn Ile Thr Ala Gln Glu Asn Gly Thr Tyr Arg Cys Tyr Phe Gln
                115                 120                 125

Glu Gly Arg Ser Tyr Asp Glu Ala Ile Leu His Leu Val Val Ala Gly
                130                 135                 140

Leu Gly Ser Lys Pro Leu Ile Ser Met Arg Gly His Glu Asp Gly Gly
145                 150                 155                 160

Ile Arg Leu Glu Cys Ile Ser Arg Gly Trp Tyr Pro Lys Pro Leu Thr
                165                 170                 175

Val Trp Arg Asp Pro Tyr Gly Gly Val Ala Pro Ala Leu Lys Glu Val
                180                 185                 190

Ser Met Pro Asp Ala Asp Gly Leu Phe Met Val Thr Thr Ala Val Ile
                195                 200                 205

Ile Arg Asp Lys Ser Val Arg Asn Met Ser Cys Ser Ile Asn Asn Thr
210                 215                 220

Leu Leu Gly Gln Lys Lys Glu Ser Val Ile Phe Ile Pro Glu Ser Phe
225                 230                 235                 240

Met Pro Ser Val Ser Pro Cys Ala Val Ala Leu Pro Ile Ile Val Val
                245                 250                 255

Ile Leu Met Ile Pro Ile Ala Val Cys Ile Tyr Trp Ile Asn Lys Leu
                260                 265                 270

Gln Lys Glu Lys Lys Ile Leu Ser Gly Glu Lys Glu Phe Glu Arg Glu
                275                 280                 285

Thr Arg Glu Ile Ala Leu Lys Glu Leu Glu Lys Glu Arg Val Gln Lys
                290                 295                 300

Glu Glu Glu Leu Gln Val Lys Glu Lys Leu Gln Glu Glu Leu Arg Trp
305                 310                 315                 320

Arg Arg Thr Phe Leu His Ala Val Asp Val Val Leu Asp Pro Asp Thr
                325                 330                 335

Ala His Pro Asp Leu Phe Leu Ser Glu Asp Arg Arg Ser Val Arg Arg
                340                 345                 350

Cys Pro Phe Arg His Leu Gly Glu Ser Val Pro Asp Asn Pro Glu Arg
                355                 360                 365

Phe Asp Ser Gln Pro Cys Val Leu Gly Arg Glu Ser Phe Ala Ser Gly
370                 375                 380

Lys His Tyr Trp Glu Val Glu Val Glu Asn Val Ile Glu Trp Thr Val
385                 390                 395                 400

Gly Val Cys Arg Asp Ser Val Glu Arg Lys Gly Glu Val Leu Leu Ile
                405                 410                 415

Pro Gln Asn Gly Phe Trp Thr Leu Glu Met His Lys Gly Gln Tyr Arg
                420                 425                 430

Ala Val Ser Ser Pro Asp Arg Ile Leu Pro Leu Lys Glu Ser Leu Cys
                435                 440                 445

Arg Val Gly Val Phe Leu Asp Tyr Glu Ala Gly Asp Val Ser Phe Tyr
                450                 455                 460

Asn Met Arg Asp Arg Ser His Ile Tyr Thr Cys Pro Arg Ser Ala Phe
465                 470                 475                 480

Ser Val Pro Val Arg Pro Phe Phe Arg Leu Gly Cys Glu Asp Ser Pro
```

```
                485                 490                 495
Ile Phe Ile Cys Pro Ala Leu Thr Gly Ala Asn Gly Val Thr Val Pro
                500                 505                 510
Glu Glu Gly Leu Thr Leu His Arg Val Gly Thr His Gln Ser Leu
            515                 520                 525

<210> SEQ ID NO 2
<211> LENGTH: 523
<212> TYPE: PRT
<213> ORGANISM: Homo sapiens

<400> SEQUENCE: 2

Met Glu Pro Ala Ala Leu His Phe Ser Leu Pro Ala Ser Leu Leu
1               5                  10                  15
Leu Leu Leu Leu Leu Leu Leu Leu Ser Leu Cys Ala Leu Val Ser Ala
                20                  25                  30
Gln Phe Thr Val Val Gly Pro Ala Asn Pro Ile Leu Ala Met Val Gly
                35                  40                  45
Glu Asn Thr Thr Leu Arg Cys His Leu Ser Pro Glu Lys Asn Ala Glu
    50                  55                  60
Asp Met Glu Val Arg Trp Phe Arg Ser Gln Phe Ser Pro Ala Val Phe
65                  70                  75                  80
Val Tyr Lys Gly Gly Arg Glu Arg Thr Glu Glu Gln Met Glu Glu Tyr
                85                  90                  95
Arg Gly Arg Ile Thr Phe Val Ser Lys Asp Ile Asn Arg Gly Ser Val
                100                 105                 110
Ala Leu Val Ile His Asn Val Thr Ala Gln Glu Asn Gly Ile Tyr Arg
                115                 120                 125
Cys Tyr Phe Gln Glu Gly Arg Ser Tyr Asp Glu Ala Ile Leu Arg Leu
                130                 135                 140
Val Val Ala Gly Leu Gly Ser Lys Pro Leu Ile Glu Ile Lys Ala Gln
145                 150                 155                 160
Glu Asp Gly Ser Ile Trp Leu Glu Cys Ile Ser Gly Gly Trp Tyr Pro
                165                 170                 175
Glu Pro Leu Thr Val Trp Arg Asp Pro Tyr Gly Glu Val Val Pro Ala
                180                 185                 190
Leu Lys Glu Val Ser Ile Ala Asp Ala Asp Gly Leu Phe Met Val Thr
                195                 200                 205
Thr Ala Val Ile Ile Arg Asp Lys Tyr Val Arg Asn Val Ser Cys Ser
                210                 215                 220
Val Asn Asn Thr Leu Leu Gly Gln Glu Lys Glu Thr Val Ile Phe Ile
225                 230                 235                 240
Pro Glu Ser Phe Met Pro Ser Ala Ser Pro Trp Met Val Ala Leu Ala
                245                 250                 255
Val Ile Leu Thr Ala Ser Pro Trp Met Val Ser Met Thr Val Ile Leu
                260                 265                 270
Ala Val Phe Ile Ile Phe Met Ala Val Ser Ile Cys Cys Ile Lys Lys
                275                 280                 285
Leu Gln Arg Glu Lys Lys Ile Leu Ser Gly Glu Lys Lys Val Glu Gln
                290                 295                 300
Glu Glu Lys Glu Ile Ala Gln Gln Leu Gln Glu Glu Leu Arg Trp Arg
305                 310                 315                 320
Arg Thr Phe Leu His Ala Ala Asp Val Val Leu Asp Pro Asp Thr Ala
                325                 330                 335
```

```
His Pro Glu Leu Phe Leu Ser Glu Asp Arg Arg Ser Val Arg Arg Gly
                340                 345                 350

Pro Tyr Arg Gln Arg Val Pro Asp Asn Pro Glu Arg Phe Asp Ser Gln
            355                 360                 365

Pro Cys Val Leu Gly Trp Glu Ser Phe Ala Ser Gly Lys His Tyr Trp
        370                 375                 380

Glu Val Glu Val Glu Asn Val Met Val Trp Thr Val Gly Val Cys Arg
385                 390                 395                 400

His Ser Val Glu Arg Lys Gly Glu Val Leu Leu Ile Pro Gln Asn Gly
                405                 410                 415

Phe Trp Thr Leu Glu Met Phe Gly Asn Gln Tyr Arg Ala Leu Ser Ser
            420                 425                 430

Pro Glu Arg Ile Leu Pro Leu Lys Glu Ser Leu Cys Arg Val Gly Val
        435                 440                 445

Phe Leu Asp Tyr Glu Ala Gly Asp Val Ser Phe Tyr Asn Met Arg Asp
        450                 455                 460

Arg Ser His Ile Tyr Thr Cys Pro Arg Ser Ala Phe Thr Val Pro Val
465                 470                 475                 480

Arg Pro Phe Phe Arg Leu Gly Ser Asp Ser Pro Ile Phe Ile Cys
                485                 490                 495

Pro Ala Leu Thr Gly Ala Ser Gly Val Met Val Pro Glu Glu Gly Leu
            500                 505                 510

Lys Leu His Arg Val Gly Thr His Gln Ser Leu
            515                 520

<210> SEQ ID NO 3
<211> LENGTH: 5
<212> TYPE: PRT
<213> ORGANISM: Homo sapiens

<400> SEQUENCE: 3

Ser Tyr Asp Ile Asn
1               5

<210> SEQ ID NO 4
<211> LENGTH: 17
<212> TYPE: PRT
<213> ORGANISM: Homo sapiens

<400> SEQUENCE: 4

Trp Ile Phe Pro Gly Asp Asp Ser Ile Ile Gln Asn Glu Lys Phe Lys
1               5                   10                  15

Gly

<210> SEQ ID NO 5
<211> LENGTH: 9
<212> TYPE: PRT
<213> ORGANISM: Homo sapiens

<400> SEQUENCE: 5

Leu Gly Pro Leu Arg Gly Phe Thr Tyr
1               5

<210> SEQ ID NO 6
<211> LENGTH: 15
<212> TYPE: PRT
<213> ORGANISM: Homo sapiens

<400> SEQUENCE: 6
```

Arg Ala Ser Glu Ser Val Asp Arg Tyr Gly Ser Ser Phe Met His
1               5                   10                  15

<210> SEQ ID NO 7
<211> LENGTH: 7
<212> TYPE: PRT
<213> ORGANISM: Homo sapiens

<400> SEQUENCE: 7

Arg Ala Ser Asn Leu Glu Ser
1               5

<210> SEQ ID NO 8
<211> LENGTH: 9
<212> TYPE: PRT
<213> ORGANISM: Homo sapiens

<400> SEQUENCE: 8

Gln Gln Ser Asn Glu Asp Pro Trp Thr
1               5

<210> SEQ ID NO 9
<211> LENGTH: 137
<212> TYPE: PRT
<213> ORGANISM: Homo sapiens

<400> SEQUENCE: 9

Met Gly Trp Ser Trp Val Phe Leu Phe Leu Leu Ser Val Thr Ala Gly
1               5                   10                  15

Val His Ser Gln Val Gln Leu Gln Gln Ser Gly Ala Glu Leu Val Lys
            20                  25                  30

Pro Gly Ala Ser Val Lys Leu Ser Cys Lys Ala Ser Gly Tyr Ile Phe
        35                  40                  45

Thr Ser Tyr Asp Ile Asn Trp Val Arg Gln Arg Pro Glu Gln Gly Leu
    50                  55                  60

Glu Trp Ile Gly Trp Ile Phe Pro Gly Asp Asp Ser Ile Ile Gln Asn
65                  70                  75                  80

Glu Lys Phe Lys Gly Lys Ala Thr Leu Thr Thr Asp Lys Ser Ser Ser
                85                  90                  95

Thr Val Tyr Met Gln Leu Ser Arg Leu Thr Ser Glu Asp Ser Ala Val
            100                 105                 110

Tyr Phe Cys Ala Arg Leu Gly Pro Leu Arg Gly Phe Thr Tyr Trp Gly
        115                 120                 125

Gln Gly Thr Leu Val Thr Val Ser Ala
    130                 135

<210> SEQ ID NO 10
<211> LENGTH: 131
<212> TYPE: PRT
<213> ORGANISM: Homo sapiens

<400> SEQUENCE: 10

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Arg Tyr Gly Ser Ser Phe Met His Trp Tyr Gln Gln Lys Pro
    50                  55                  60

Gly Gln Pro Pro Lys Leu Leu Ile Tyr Arg Ala Ser Asn Leu Glu Ser
65                  70                  75                  80

Gly Ile Pro Ala Arg Phe Ser Gly Ser Gly Ser Arg Thr Asp Phe Thr
                85                  90                  95

Leu Thr Ile Asn Pro Val Glu Ala Asp Asp Val Ala Tyr Tyr Cys
            100                 105                 110

Gln Gln Ser Asn Glu Asp Pro Trp Thr Phe Gly Gly Gly Thr Lys Leu
        115                 120                 125

Glu Ile Lys
    130

<210> SEQ ID NO 11
<211> LENGTH: 5
<212> TYPE: PRT
<213> ORGANISM: Homo sapiens

<400> SEQUENCE: 11

Asp Tyr Ser Met Asn
1               5

<210> SEQ ID NO 12
<211> LENGTH: 17
<212> TYPE: PRT
<213> ORGANISM: Homo sapiens

<400> SEQUENCE: 12

Arg Ile Asn Thr Glu Thr Gly Glu Pro Thr Tyr Ala Asp Asp Phe Lys
1               5                   10                  15

Gly

<210> SEQ ID NO 13
<211> LENGTH: 5
<212> TYPE: PRT
<213> ORGANISM: Homo sapiens

<400> SEQUENCE: 13

Asp Tyr Ala Lys Arg
1               5

<210> SEQ ID NO 14
<211> LENGTH: 11
<212> TYPE: PRT
<213> ORGANISM: Homo sapiens

<400> SEQUENCE: 14

Lys Ala Ser Gln Asp Val Ile Thr Ala Val Ala
1               5                   10

<210> SEQ ID NO 15
<211> LENGTH: 7
<212> TYPE: PRT
<213> ORGANISM: Homo sapiens

<400> SEQUENCE: 15

Ser Thr Ser Tyr Arg Tyr Thr
1               5

<210> SEQ ID NO 16
<211> LENGTH: 9
<212> TYPE: PRT
<213> ORGANISM: Homo sapiens

<400> SEQUENCE: 16

Leu Gln His Tyr Thr Thr Pro Trp Thr
1               5

<210> SEQ ID NO 17
<211> LENGTH: 133
<212> TYPE: PRT
<213> ORGANISM: Homo sapiens

<400> SEQUENCE: 17

Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asp Tyr Ser Met Asn Trp Val Lys Gln Ala Pro Gly Lys Gly Leu
    50                  55                  60

Lys Trp Val Gly Arg Ile Asn Thr Glu Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Lys Asn Leu Lys Asn Glu Asp Thr Ala Thr
            100                 105                 110

Tyr Phe Cys Val Arg Asp Tyr Ala Lys Arg Trp Gly Gln Gly Thr Ser
        115                 120                 125

Val Thr Val Ser Ser
    130

<210> SEQ ID NO 18
<211> LENGTH: 131
<212> TYPE: PRT
<213> ORGANISM: Homo sapiens

<400> SEQUENCE: 18

Met Gly Ile Lys Met Glu Ser Gln Ile Gln Val Phe Val Phe Val Ser
1               5                   10                  15

Leu Trp Leu Ser Gly Val Asp Gly Asp Ile Val Met Thr Gln Ser His
            20                  25                  30

Lys Phe Met Ser Thr Ser Val Gly Asp Arg Val Ser Ile Thr Cys Lys
        35                  40                  45

Ala Ser Gln Asp Val Ile Thr Ala Val Ala Trp Tyr Gln Gln Lys Pro
    50                  55                  60

Gly Gln Ser Pro Lys Leu Leu Ile Tyr Ser Thr Ser Tyr Arg Tyr Thr
65                  70                  75                  80

Gly Val Pro Asp Arg Phe Thr Gly Ser Gly Ser Gly Thr Asp Phe Thr
                85                  90                  95

Phe Thr Ile Ser Ser Val Gln Ala Glu Asp Leu Ala Val Tyr Tyr Cys
            100                 105                 110

Leu Gln His Tyr Thr Thr Pro Trp Thr Phe Gly Gly Gly Thr Lys Leu
        115                 120                 125

Glu Ile Lys
    130

<210> SEQ ID NO 19
<211> LENGTH: 5
<212> TYPE: PRT

```
<213> ORGANISM: Homo sapiens

<400> SEQUENCE: 19

Ser Tyr Trp Ile Glu
1               5

<210> SEQ ID NO 20
<211> LENGTH: 17
<212> TYPE: PRT
<213> ORGANISM: Homo sapiens

<400> SEQUENCE: 20

Glu Ile Leu Pro Gly Ser Gly Ser Thr Lys Tyr Asn Glu Lys Phe Arg
1               5                   10                  15

Gly

<210> SEQ ID NO 21
<211> LENGTH: 12
<212> TYPE: PRT
<213> ORGANISM: Homo sapiens

<400> SEQUENCE: 21

Leu Lys Gly Tyr Tyr Gly Gly Gly Ala Met Asp Tyr
1               5                   10

<210> SEQ ID NO 22
<211> LENGTH: 11
<212> TYPE: PRT
<213> ORGANISM: Homo sapiens

<400> SEQUENCE: 22

Arg Ala Ser Lys Ser Ile Ser Lys Tyr Leu Ala
1               5                   10

<210> SEQ ID NO 23
<211> LENGTH: 7
<212> TYPE: PRT
<213> ORGANISM: Homo sapiens

<400> SEQUENCE: 23

Ser Gly Ser Thr Leu Gln Ser
1               5

<210> SEQ ID NO 24
<211> LENGTH: 9
<212> TYPE: PRT
<213> ORGANISM: Homo sapiens

<400> SEQUENCE: 24

Gln Gln His Asn Glu Tyr Pro Trp Thr
1               5

<210> SEQ ID NO 25
<211> LENGTH: 140
<212> TYPE: PRT
<213> ORGANISM: Homo sapiens

<400> SEQUENCE: 25

Met Glu Trp Thr Trp Val Phe Leu Phe Leu Leu Ser Val Thr Ala Gly
1               5                   10                  15

Val His Ser Gln Val His Leu Gln Gln Ser Gly Ala Glu Leu Met Lys
                20                  25                  30

Pro Gly Ala Ser Val Lys Ile Ser Cys Lys Ala Thr Gly Tyr Thr Phe
```

```
            35                  40                  45
Ser Ser Tyr Trp Ile Glu Trp Val Lys Gln Arg Pro Gly His Gly Arg
 50                  55                  60

Glu Trp Ile Gly Glu Ile Leu Pro Gly Ser Gly Ser Thr Lys Tyr Asn
 65                  70                  75                  80

Glu Lys Phe Arg Gly Lys Ala Thr Phe Ala Ala Asp Thr Ser Ser Asn
                 85                  90                  95

Thr Ala Tyr Val Gln Leu Ser Ser Leu Thr Ser Glu Asp Ser Ala Val
                100                 105                 110

Tyr Tyr Cys Ala Arg Leu Lys Gly Tyr Gly Gly Ala Met Asp
                115                 120                 125

Tyr Trp Gly Gln Gly Thr Ser Val Thr Val Ser Ser
130                 135                 140
```

<210> SEQ ID NO 26
<211> LENGTH: 127
<212> TYPE: PRT
<213> ORGANISM: Homo sapiens

<400> SEQUENCE: 26

```
Met Arg Phe Gln Val Gln Val Leu Gly Leu Leu Leu Leu Trp Ile Ser
 1               5                  10                  15

Gly Ala Gln Cys Asp Val Gln Ile Thr Gln Ser Pro Ser Tyr Leu Ala
                20                  25                  30

Ala Ser Pro Gly Glu Thr Ile Thr Ile Asn Cys Arg Ala Ser Lys Ser
                35                  40                  45

Ile Ser Lys Tyr Leu Ala Trp Tyr Gln Glu Lys Pro Gly Lys Thr Asn
 50                  55                  60

Glu Leu Leu Ile Tyr Ser Gly Ser Thr Leu Gln Ser Gly Ile Pro Ser
 65                  70                  75                  80

Arg Phe Ser Gly Ser Gly Ser Gly Thr Asp Phe Thr Leu Thr Ile Ser
                 85                  90                  95

Ser Leu Glu Pro Glu Asp Phe Ala Met Tyr Tyr Cys Gln Gln His Asn
                100                 105                 110

Glu Tyr Pro Trp Thr Phe Gly Gly Gly Thr Lys Leu Glu Ile Lys
                115                 120                 125
```

<210> SEQ ID NO 27
<211> LENGTH: 5
<212> TYPE: PRT
<213> ORGANISM: Homo sapiens

<400> SEQUENCE: 27

```
Asp Phe Tyr Met Tyr
 1               5
```

<210> SEQ ID NO 28
<211> LENGTH: 17
<212> TYPE: PRT
<213> ORGANISM: Homo sapiens

<400> SEQUENCE: 28

```
Thr Ile Ser Asp Gly Gly Ser His Thr Tyr Tyr Pro Asp Ser Val Lys
 1               5                  10                  15

Gly
```

<210> SEQ ID NO 29
<211> LENGTH: 8

<212> TYPE: PRT
<213> ORGANISM: Homo sapiens

<400> SEQUENCE: 29

Asp Thr Thr Ile Ile Thr Pro Tyr
1               5

<210> SEQ ID NO 30
<211> LENGTH: 14
<212> TYPE: PRT
<213> ORGANISM: Homo sapiens

<400> SEQUENCE: 30

Arg Ser Ser Thr Gly Ala Val Thr Thr Ser Asn Tyr Ala Asn
1               5                   10

<210> SEQ ID NO 31
<211> LENGTH: 7
<212> TYPE: PRT
<213> ORGANISM: Homo sapiens

<400> SEQUENCE: 31

Gly Thr Asn Asn Arg Ala Pro
1               5

<210> SEQ ID NO 32
<211> LENGTH: 9
<212> TYPE: PRT
<213> ORGANISM: Homo sapiens

<400> SEQUENCE: 32

Gly Leu Trp Tyr Ser Asn His Trp Val
1               5

<210> SEQ ID NO 33
<211> LENGTH: 136
<212> TYPE: PRT
<213> ORGANISM: Homo sapiens

<400> SEQUENCE: 33

Met Asn Phe Gly Leu Ser Leu Ile Phe Leu Val Leu Val Leu Lys Gly
1               5                   10                  15

Val Gln Cys Glu Val Gln Leu Val Glu Ser Gly Gly Asp Leu Val Lys
                20                  25                  30

Pro Gly Gly Ser Leu Lys Leu Ser Cys Ala Ala Ser Gly Phe Thr Phe
            35                  40                  45

Ser Asp Phe Tyr Met Tyr Trp Val Arg Arg Thr Pro Glu Lys Arg Leu
        50                  55                  60

Glu Trp Val Ala Thr Ile Ser Asp Gly Gly Ser His Thr Tyr Tyr Pro
65                  70                  75                  80

Asp Ser Val Lys Gly Arg Phe Thr Ile Ser Arg Asp Asn Ala Lys Asn
                85                  90                  95

Asn Leu Tyr Leu Gln Met Arg Ser Leu Lys Ser Glu Asp Thr Ala Met
            100                 105                 110

Tyr Tyr Cys Gly Arg Asp Thr Thr Ile Ile Thr Pro Tyr Trp Gly Gln
        115                 120                 125

Gly Thr Leu Val Thr Val Ser Ala
    130                 135

<210> SEQ ID NO 34
<211> LENGTH: 128

<212> TYPE: PRT
<213> ORGANISM: Homo sapiens

<400> SEQUENCE: 34

Met Ala Trp Ile Ser Leu Ile Leu Ser Leu Leu Ala Leu Ser Ser Gly
1               5                   10                  15

Ala Ile Ser Gln Ser Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Asn Asn Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Gly Leu Trp
            100                 105                 110

Tyr Ser Asn His Trp Val Phe Gly Gly Gly Thr Lys Leu Thr Val Leu
        115                 120                 125

<210> SEQ ID NO 35
<211> LENGTH: 5
<212> TYPE: PRT
<213> ORGANISM: Homo sapiens

<400> SEQUENCE: 35

Gly Tyr Trp Met Thr
1               5

<210> SEQ ID NO 36
<211> LENGTH: 17
<212> TYPE: PRT
<213> ORGANISM: Homo sapiens

<400> SEQUENCE: 36

Glu Ile Asn Pro Asp Ser Ser Thr Ile Asn Tyr Thr Pro Ser Leu Arg
1               5                   10                  15

Asp

<210> SEQ ID NO 37
<211> LENGTH: 7
<212> TYPE: PRT
<213> ORGANISM: Homo sapiens

<400> SEQUENCE: 37

Gly Ser Tyr Tyr Pro Ser Tyr
1               5

<210> SEQ ID NO 38
<211> LENGTH: 15
<212> TYPE: PRT
<213> ORGANISM: Homo sapiens

<400> SEQUENCE: 38

Arg Ala Ser Lys Ser Val Ser Ser Ser Gly Tyr Ser Tyr Met Asn
1               5                   10                  15

<210> SEQ ID NO 39
<211> LENGTH: 7
<212> TYPE: PRT

<213> ORGANISM: Homo sapiens

<400> SEQUENCE: 39

Leu Ala Ser Asn Leu Glu Ser
1               5

<210> SEQ ID NO 40
<211> LENGTH: 9
<212> TYPE: PRT
<213> ORGANISM: Homo sapiens

<400> SEQUENCE: 40

Gln His Ser Arg Glu Leu Pro His Thr
1               5

<210> SEQ ID NO 41
<211> LENGTH: 134
<212> TYPE: PRT
<213> ORGANISM: Homo sapiens

<400> SEQUENCE: 41

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Gly Tyr Trp Met Thr Trp Val Arg Gln Ala Pro Gly Lys Gly Leu Glu
    50                  55                  60

Trp Ile Gly Glu Ile Asn Pro Asp Ser Ser Thr Ile Asn Tyr Thr Pro
65                  70                  75                  80

Ser Leu Arg Asp Lys Phe Ile Ile Ser Arg Asp Asn Ala Lys Asn Thr
                85                  90                  95

Leu Tyr Leu Gln Met Ser Lys Val Arg Ser Glu Asp Thr Ala Leu Tyr
            100                 105                 110

Phe Cys Ala Arg Gly Ser Tyr Tyr Pro Ser Tyr Trp Gly Gln Gly Thr
        115                 120                 125

Leu Val Thr Val Ser Ala
    130

<210> SEQ ID NO 42
<211> LENGTH: 131
<212> TYPE: PRT
<213> ORGANISM: Homo sapiens

<400> SEQUENCE: 42

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45

Val Ser Ser Ser Gly Tyr Ser Tyr Met Asn Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Asp Glu Asp Ala Ala Thr Tyr Tyr Cys
            100                 105                 110

Gln His Ser Arg Glu Leu Pro His Thr Phe Gly Gly Gly Thr Lys Leu
        115                 120                 125

Glu Ile Lys
    130

<210> SEQ ID NO 43
<211> LENGTH: 5
<212> TYPE: PRT
<213> ORGANISM: Homo sapiens

<400> SEQUENCE: 43

Gly Tyr Trp Met Thr
1               5

<210> SEQ ID NO 44
<211> LENGTH: 17
<212> TYPE: PRT
<213> ORGANISM: Homo sapiens

<400> SEQUENCE: 44

Glu Ile Asn Pro Asp Ser Ser Thr Ile Asn Tyr Thr Pro Ser Leu Arg
1               5                   10                  15

Asp

<210> SEQ ID NO 45
<211> LENGTH: 7
<212> TYPE: PRT
<213> ORGANISM: Homo sapiens

<400> SEQUENCE: 45

Gly Ser Tyr Tyr Pro Ser Tyr
1               5

<210> SEQ ID NO 46
<211> LENGTH: 15
<212> TYPE: PRT
<213> ORGANISM: Homo sapiens

<400> SEQUENCE: 46

Arg Ala Ser Lys Ser Val Ser Ser Ser Gly Tyr Ser Tyr Met Asn
1               5                   10                  15

<210> SEQ ID NO 47
<211> LENGTH: 7
<212> TYPE: PRT
<213> ORGANISM: Homo sapiens

<400> SEQUENCE: 47

Leu Ala Ser Asn Leu Glu Ser
1               5

<210> SEQ ID NO 48
<211> LENGTH: 9
<212> TYPE: PRT
<213> ORGANISM: Homo sapiens

<400> SEQUENCE: 48

Gln His Ser Arg Glu Leu Pro His Thr
1               5

<210> SEQ ID NO 49

```
<211> LENGTH: 134
<212> TYPE: PRT
<213> ORGANISM: Homo sapiens

<400> SEQUENCE: 49

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Gly Tyr Trp Met Thr Trp Val Arg Gln Ala Pro Gly Lys Gly Leu Glu
    50                  55                  60

Trp Ile Gly Glu Ile Asn Pro Asp Ser Ser Thr Ile Asn Tyr Thr Pro
65                  70                  75                  80

Ser Leu Arg Asp Lys Phe Ile Ile Ser Arg Asp Asn Ala Lys Asn Thr
                85                  90                  95

Leu Tyr Leu Gln Met Ser Lys Val Arg Ser Glu Asp Thr Ala Leu Tyr
            100                 105                 110

Phe Cys Ala Arg Gly Ser Tyr Tyr Pro Ser Tyr Trp Gly Gln Gly Thr
        115                 120                 125

Leu Val Thr Val Ser Ala
    130

<210> SEQ ID NO 50
<211> LENGTH: 131
<212> TYPE: PRT
<213> ORGANISM: Homo sapiens

<400> SEQUENCE: 50

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45

Val Ser Ser Ser Gly Tyr Ser Tyr Met Asn Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Asp Glu Asp Ala Ala Thr Tyr Tyr Cys
            100                 105                 110

Gln His Ser Arg Glu Leu Pro His Thr Phe Gly Gly Gly Thr Lys Leu
        115                 120                 125

Glu Ile Lys
    130

<210> SEQ ID NO 51
<211> LENGTH: 6
<212> TYPE: PRT
<213> ORGANISM: Homo sapiens

<400> SEQUENCE: 51

Ser Gly Tyr Tyr Trp Asn
1               5
```

<210> SEQ ID NO 52
<211> LENGTH: 16
<212> TYPE: PRT
<213> ORGANISM: Homo sapiens

<400> SEQUENCE: 52

Tyr Ile Ser Tyr Asp Gly Asn Asn Asn Tyr Asn Pro Ser Leu Lys Asn
1               5                   10                  15

<210> SEQ ID NO 53
<211> LENGTH: 12
<212> TYPE: PRT
<213> ORGANISM: Homo sapiens

<400> SEQUENCE: 53

Pro Leu Tyr Asp Gly Tyr Tyr Trp Tyr Phe Asp Val
1               5                   10

<210> SEQ ID NO 54
<211> LENGTH: 11
<212> TYPE: PRT
<213> ORGANISM: Homo sapiens

<400> SEQUENCE: 54

Ile Thr Ser Thr Asp Ile Asp Asp Met Asn
1               5                   10

<210> SEQ ID NO 55
<211> LENGTH: 7
<212> TYPE: PRT
<213> ORGANISM: Homo sapiens

<400> SEQUENCE: 55

Glu Ala Asn Thr Leu Arg Pro
1               5

<210> SEQ ID NO 56
<211> LENGTH: 9
<212> TYPE: PRT
<213> ORGANISM: Homo sapiens

<400> SEQUENCE: 56

Leu Gln Ser Asp Asn Leu Pro Tyr Thr
1               5

<210> SEQ ID NO 57
<211> LENGTH: 139
<212> TYPE: PRT
<213> ORGANISM: Homo sapiens

<400> SEQUENCE: 57

Met Lys Val Leu Ser Leu Leu Tyr Leu Leu Thr Ala Ile Pro Gly Ile
1               5                   10                  15

Leu Ser Asp Val Gln Leu Gln Glu Ser Gly Pro Gly Leu Val Lys Pro
                20                  25                  30

Ser Gln Ser Leu Ser Leu Thr Cys Ser Val Thr Gly Tyr Ser Ile Thr
            35                  40                  45

Ser Gly Tyr Tyr Trp Asn Trp Ile Arg Gln Phe Pro Gly Asn Lys Leu
        50                  55                  60

Glu Trp Met Gly Tyr Ile Ser Tyr Asp Gly Asn Asn Asn Tyr Asn Pro
65                  70                  75                  80

Ser Leu Lys Asn Arg Ile Ser Ile Thr Arg Asp Thr Ser Lys Asn Gln 85                  90                  95
Phe Phe Leu Lys Leu Asn Ser Val Thr Thr Glu Asp Thr Ala Thr Tyr
                100                 105                 110

Tyr Cys Ala Ser Pro Leu Tyr Asp Gly Tyr Tyr Trp Tyr Phe Asp Val
            115                 120                 125

Trp Gly Ala Gly Thr Thr Val Thr Val Ser Ser
        130                 135

<210> SEQ ID NO 58
<211> LENGTH: 129
<212> TYPE: PRT
<213> ORGANISM: Homo sapiens

<400> SEQUENCE: 58

Met Thr Met Phe Ser Leu Ala Leu Leu Ser Leu Leu Leu Leu Cys
1               5                   10                  15

Val Ser Asp Ser Arg Ala Glu Thr Thr Val Thr Gln Ser Pro Ala Ser
                20                  25                  30

Leu Ser Leu Ala Ile Gly Glu Lys Val Thr Ile Arg Cys Ile Thr Ser
            35                  40                  45

Thr Asp Ile Asp Asp Asp Met Asn Trp Tyr Gln Gln Lys Pro Gly Glu
        50                  55                  60

Pro Pro Lys Leu Leu Ile Ser Glu Ala Asn Thr Leu Arg Pro Gly Val
65                  70                  75                  80

Pro Ser Arg Phe Ser Ser Gly Arg Gly Thr Asp Phe Val Phe Thr
                85                  90                  95

Ile Glu Asn Met Leu Ser Glu Asp Val Ala Asp Tyr Tyr Cys Leu Gln
                100                 105                 110

Ser Asp Asn Leu Pro Tyr Thr Phe Gly Gly Gly Thr Lys Leu Glu Ile
            115                 120                 125

Lys

<210> SEQ ID NO 59
<211> LENGTH: 15
<212> TYPE: DNA
<213> ORGANISM: Homo sapiens

<400> SEQUENCE: 59
agctatgata taaac                                                15

<210> SEQ ID NO 60
<211> LENGTH: 51
<212> TYPE: DNA
<213> ORGANISM: Homo sapiens

<400> SEQUENCE: 60 tggattttc ctggagatga tagtattatt cagaatgaga agttcaaggg c          51

<210> SEQ ID NO 61
<211> LENGTH: 27
<212> TYPE: DNA
<213> ORGANISM: Homo sapiens

<400> SEQUENCE: 61
ttgggcccat tacgagggtt tacttac                                   27

<210> SEQ ID NO 62
<211> LENGTH: 45
<212> TYPE: DNA

<213> ORGANISM: Homo sapiens

<400> SEQUENCE: 62

| agagccagtg aaagtgttga tcgttatggc agtagtttta tgcac | 45 |

<210> SEQ ID NO 63
<211> LENGTH: 21
<212> TYPE: DNA
<213> ORGANISM: Homo sapiens

<400> SEQUENCE: 63

| cgtgcatcca acctagaatc t | 21 |

<210> SEQ ID NO 64
<211> LENGTH: 27
<212> TYPE: DNA
<213> ORGANISM: Homo sapiens

<400> SEQUENCE: 64

| cagcaaagta atgaggatcc gtggacg | 27 |

<210> SEQ ID NO 65
<211> LENGTH: 456
<212> TYPE: DNA
<213> ORGANISM: Homo sapiens

<400> SEQUENCE: 65

| atgggatgga gctgggtctt tctcttcctc ctgtcagtaa ctgcaggtgt ccactcccag | 60 |
| gttcagctgc agcagtctgg agctgaactg gtaaagcctg gggcttcagt gaagttgtcc | 120 |
| tgcaaggctt ctggctacat cttcacaagc tatgatataa actgggtgag gcagaggcct | 180 |
| gaacaggac ttgagtggat tggatggatt tttcctggag atgatagtat tattcagaat | 240 |
| gagaagttca gggcaaggc cacactgact acagacaaat cctccagcac agtctacatg | 300 |
| cagctcagca ggctgacatc tgaggactct gctgtctatt tctgtgcaag attgggccca | 360 |
| ttacgagggt ttacttactg ggccaagggg actctggtca ctgtctctgc agggtttact | 420 |
| tactggggcc aagggactct ggtcactgtc tctgca | 456 |

<210> SEQ ID NO 66
<211> LENGTH: 393
<212> TYPE: DNA
<213> ORGANISM: Homo sapiens

<400> SEQUENCE: 66

| atggagacag acacactcct gctatgggtg ctgctgctct gggttccagg ttccacaggt | 60 |
| gacattgtgc tgacccaatc tccagcttct ttggctgtgt ctctagggca gagggccacc | 120 |
| atatcctgca gagccagtga aagtgttgat cgttatggca gtagttttat gcactggtac | 180 |
| cagcagaaac caggacagcc acccaaactc ctcatctatc gtgcatccaa cctagaatct | 240 |
| gggatccctg ccaggttcag tggcagtggg tctaggacag acttcaccct caccattaat | 300 |
| cctgtggagg ctgatgatgt tgcaacctat tactgtcagc aaagtaatga ggatccgtgg | 360 |
| acgttcggtg aggcaccaa gctggaaatc aaa | 393 |

<210> SEQ ID NO 67
<211> LENGTH: 15
<212> TYPE: DNA
<213> ORGANISM: Homo sapiens

<400> SEQUENCE: 67
gactattcaa tgaac                                           15

<210> SEQ ID NO 68
<211> LENGTH: 51
<212> TYPE: DNA
<213> ORGANISM: Homo sapiens

<400> SEQUENCE: 68
aggatcaaca ctgagactgg tgagccaaca tatgcagatg acttcaaggg a     51

<210> SEQ ID NO 69
<211> LENGTH: 15
<212> TYPE: DNA
<213> ORGANISM: Homo sapiens

<400> SEQUENCE: 69
gactacgcta agcgg                                           15

<210> SEQ ID NO 70
<211> LENGTH: 33
<212> TYPE: DNA
<213> ORGANISM: Homo sapiens

<400> SEQUENCE: 70
aaggccagtc aggatgtgat tactgctgta gcc                       33

<210> SEQ ID NO 71
<211> LENGTH: 21
<212> TYPE: DNA
<213> ORGANISM: Homo sapiens

<400> SEQUENCE: 71
tcgacatcct accggtacac t                                    21

<210> SEQ ID NO 72
<211> LENGTH: 27
<212> TYPE: DNA
<213> ORGANISM: Homo sapiens

<400> SEQUENCE: 72
ctgcaacatt atactactcc gtggacg                              27

<210> SEQ ID NO 73
<211> LENGTH: 399
<212> TYPE: DNA
<213> ORGANISM: Homo sapiens

<400> SEQUENCE: 73
atggcttggg tgtggacctt gctattcctg atggcagctg cccaaagtat ccaagcacag    60
atccagttgg tacagtctgg acctgagctg aagaagcctg agagacagt caagatctcc    120 tgcaaggctt ctggttatac cttcacagac tattcaatga actgggtgaa acaggctcca    180
ggaaagggtt taaagtgggt gggcaggatc aacactgaga ctggtgagcc aacatatgca    240
gatgacttca agggacggtt tgccttctct ttggaaacct ctgccagcac tgcctatttg    300
cagatcaaaa acctcaaaaa tgaggacacg gctacatatt tctgtgttag agactacgct    360
aagcggtggg gtcaaggaac ctcagtcacc gtctcctca                 399

<210> SEQ ID NO 74
<211> LENGTH: 393
<212> TYPE: DNA

<213> ORGANISM: Homo sapiens

<400> SEQUENCE: 74

| | | | | | |
|---|---|---|---|---|---|
| atgggcatca | aaatggagtc | acagattcag | gtctttgtat | tcgtgtctct | ctggttgtct | 60 |
| ggtgttgacg | gagacattgt | gatgacccag | tctcacaaat | tcatgtccac | atcagtagga | 120 |
| gacagggtca | gcatcacctg | caaggccagt | caggatgtga | ttactgctgt | agcctggtat | 180 |
| caacagaaac | caggacaatc | tcctaaacta | ctgatttact | cgacatccta | ccggtacact | 240 |
| ggagtccctg | atcgcttcac | tggcagtgga | tctgggacgg | atttcacttt | caccatcagc | 300 |
| agtgtgcagg | ctgaagacct | ggcagtttat | tactgtctgc | aacattatac | tactccgtgg | 360 |
| acgttcggtg | gaggcaccaa | gctggaaatc | aaa | | | 393 |

<210> SEQ ID NO 75
<211> LENGTH: 15
<212> TYPE: DNA
<213> ORGANISM: Homo sapiens

<400> SEQUENCE: 75
agctactgga tagag                                              15

<210> SEQ ID NO 76
<211> LENGTH: 51
<212> TYPE: DNA
<213> ORGANISM: Homo sapiens

<400> SEQUENCE: 76 gagatttttac ctggaagtgg aagtactaag tacaatgaga agtttagggg c     51

<210> SEQ ID NO 77
<211> LENGTH: 36
<212> TYPE: DNA
<213> ORGANISM: Homo sapiens

<400> SEQUENCE: 77
ttgaagggtt actacggagg aggtgctatg gactac                       36

<210> SEQ ID NO 78
<211> LENGTH: 33
<212> TYPE: DNA
<213> ORGANISM: Homo sapiens

<400> SEQUENCE: 78
agggcaagta agagcattag caaatattta gcc                          33

<210> SEQ ID NO 79
<211> LENGTH: 21
<212> TYPE: DNA
<213> ORGANISM: Homo sapiens

<400> SEQUENCE: 79
tctggatcca ctttgcaatc t                                       21

<210> SEQ ID NO 80
<211> LENGTH: 27
<212> TYPE: DNA
<213> ORGANISM: Homo sapiens

<400> SEQUENCE: 80
caacagcata atgaataccc gtggacg                                 27

<210> SEQ ID NO 81
<211> LENGTH: 420
<212> TYPE: DNA
<213> ORGANISM: Homo sapiens

<400> SEQUENCE: 81

```
atggaatgga cctgggtctt tctcttcctc ctgtcagtaa ctgcaggtgt ccactcccag      60
gttcacctgc agcagtctgg agctgagctg atgaagcctg gggcctcagt gaaaatatcc     120
tgcaaggcta ctggctacac attcagtagc tactggatag agtgggtaaa gcagaggcct     180
ggacatggcc gtgagtggat tggagagatt ttacctggaa gtggaagtac taagtacaat     240
gagaagttta ggggcaaggc cacattcgct gcagatacat cctccaacac agcctacgtg     300
caactcagca gcctgacatc tgaggactct gccgtctatt actgtgcaag attgaagggt     360
tactacggag aggtgctat ggactactgg ggtcaaggaa cctcagttac cgtctcttca      420
```

<210> SEQ ID NO 82
<211> LENGTH: 381
<212> TYPE: DNA
<213> ORGANISM: Homo sapiens

<400> SEQUENCE: 82

```
atgaggttcc aggttcaggt tctggggctc cttctgctct ggatatcagg tgcccagtgt      60
gatgtccaga taacccagtc tccatcttat cttgctgcat ctcctggaga aaccattact     120
attaattgca gggcaagtaa gagcattagc aaatatttag cctggtatca agagaaacct     180
gggaaaacta atgagcttct tatctactct ggatccactt tgcaatctgg aattccatca     240
aggttcagtg gcagtggatc tggtacagat ttcactctca ccatcagtag cctggagcct     300
gaagattttg caatgtatta ctgtcaacag cataatgaat acccgtggac gttcggtgga     360
ggcaccaagc tggaaatcaa a                                                381
```

<210> SEQ ID NO 83
<211> LENGTH: 15
<212> TYPE: DNA
<213> ORGANISM: Homo sapiens

<400> SEQUENCE: 83

```
gacttttaca tgtat                                                       15
```

<210> SEQ ID NO 84
<211> LENGTH: 51
<212> TYPE: DNA
<213> ORGANISM: Homo sapiens

<400> SEQUENCE: 84

```
accattagtg atggtggtag tcacacctac tatccagaca gtgtgaaggg g              51
```

<210> SEQ ID NO 85
<211> LENGTH: 24
<212> TYPE: DNA
<213> ORGANISM: Homo sapiens

<400> SEQUENCE: 85

```
gatactacga taattactcc ttac                                             24
```

<210> SEQ ID NO 86
<211> LENGTH: 42
<212> TYPE: DNA
<213> ORGANISM: Homo sapiens

<400> SEQUENCE: 86
cgctcaagta ctggggctgt tacaactagt aactatgcca ac        42

<210> SEQ ID NO 87
<211> LENGTH: 21
<212> TYPE: DNA
<213> ORGANISM: Homo sapiens

<400> SEQUENCE: 87
ggtaccaaca accgagctcc a        21

<210> SEQ ID NO 88
<211> LENGTH: 27
<212> TYPE: DNA
<213> ORGANISM: Homo sapiens

<400> SEQUENCE: 88
ggtctttggt acagcaacca ttgggtg        27

<210> SEQ ID NO 89
<211> LENGTH: 408
<212> TYPE: DNA
<213> ORGANISM: Homo sapiens

<400> SEQUENCE: 89
atgaacttcg ggctcagctt gattttcctt gtccttgttt taaaaggtgt ccagtgtgaa        60
gtgcagctgg tggagtctgg gggagactta gtgaagcctg agggtccct gaaactctcc        120
tgtgcagcct ctggattcac tttcagtgac ttttacatgt attgggttcg ccggactccg        180
gaaaagaggc tggagtgggt cgcaaccatt agtgatggtg gtagtcacac ctactatcca        240
gacagtgtga agggccgatt caccatctcc agagacaatg ccaagaacaa cctctaccta        300
caaatgagaa gtctgaagtc tgaggacaca gccatgtatt actgtggaag agatactacg        360
ataattactc cttactgggg ccaagggact ctggtcactg tctctgca        408

<210> SEQ ID NO 90
<211> LENGTH: 384
<212> TYPE: DNA
<213> ORGANISM: Homo sapiens

<400> SEQUENCE: 90
atggcctgga tttcacttat actctctctc ctggctctca gctcagggc catttcccag        60
tctgttgtga ctcaggaatc tgcactcacc acatcacctg gtgaaacagt cacactcact        120
tgtcgctcaa gtactggggc tgttacaact agtaactatg ccaactgggt ccaagaaaaa        180
ccagatcatt tattcactgg tctaataggt ggtaccaaca accgagctcc aggtgttcct        240
gccagattct caggctccct gattggagac aaggctgccc tcaccatcac aggggcacag        300
actgaggatg aggcaatata tttctgtggt ctttggtaca gcaaccattg ggtgttcggt        360
ggaggaacca aactgactgt ccta        384

<210> SEQ ID NO 91
<211> LENGTH: 15
<212> TYPE: DNA
<213> ORGANISM: Homo sapiens

<400> SEQUENCE: 91
ggatactgga tgact        15

```
<210> SEQ ID NO 92
<211> LENGTH: 51
<212> TYPE: DNA
<213> ORGANISM: Homo sapiens

<400> SEQUENCE: 92
gaaattaatc cagatagcag tacgataaac tatacgccat ctctaaggga t            51

<210> SEQ ID NO 93
<211> LENGTH: 21
<212> TYPE: DNA
<213> ORGANISM: Homo sapiens

<400> SEQUENCE: 93
gggagctact atccctctta c                                             21

<210> SEQ ID NO 94
<211> LENGTH: 45
<212> TYPE: DNA
<213> ORGANISM: Homo sapiens

<400> SEQUENCE: 94
agggccagca aaagtgtcag ttcatctggc tatagttata tgaac                   45

<210> SEQ ID NO 95
<211> LENGTH: 21
<212> TYPE: DNA
<213> ORGANISM: Homo sapiens

<400> SEQUENCE: 95
cttgcatcca acctagaatc t                                             21

<210> SEQ ID NO 96
<211> LENGTH: 27
<212> TYPE: DNA
<213> ORGANISM: Homo sapiens

<400> SEQUENCE: 96
cagcacagta gggagcttcc gcacacg                                       27

<210> SEQ ID NO 97
<211> LENGTH: 402
<212> TYPE: DNA
<213> ORGANISM: Homo sapiens

<400> SEQUENCE: 97
atggattttg ggctgatttt ttttattgtt gctcttttaa aaggggtcca gtgtgaagtg    60
aagcttctcg agtctggagg tggcctggtg cagcctggag gatccctgaa actctcctgt   120
gcagcctcag gattcgattt tagtggatac tggatgactt gggtccggca ggctccaggg   180
aaagggctag aatggattgg agaaattaat ccagatagca gtacgataaa ctatacgcca   240
tctctaaggg ataaattcat catctccaga gacaacgcca gaatacgct gtacctgcaa    300 atgagcaaag tgagatctga ggacacagcc ctttatttct gtgcaagagg gagctactat   360
ccctcttact ggggccaagg gactctggtc actgtctctg ca                      402

<210> SEQ ID NO 98
<211> LENGTH: 393
<212> TYPE: DNA
<213> ORGANISM: Homo sapiens

<400> SEQUENCE: 98
```

-continued

```
atggagacag acacactcct gttatgggta ctgctgctct gggttccagg ttccactggg      60
gacattgtgc tgacacagtc tcctgcttcc ttagctgtat ctctgggca gagggccacc     120 atctcatgca gggccagcaa aagtgtcagt tcatctggct atagttatat gaactggtac    180
cagcagaaac caggacagcc acccaaactc ctcatctatc ttgcatccaa cctagaatct    240
ggggtccctg ccaggttcag tggcagtggg tctgggacag acttcaccct caacatccat    300
cctgtggagg atgaggatgc tgcaacctat tactgtcagc acagtaggga gcttccgcac    360
acgttcggag gggggaccaa gctggaaata aaa                                 393
```

<210> SEQ ID NO 99
<211> LENGTH: 15
<212> TYPE: DNA
<213> ORGANISM: Homo sapiens

<400> SEQUENCE: 99

```
ggatactgga tgact                                                      15
```

<210> SEQ ID NO 100
<211> LENGTH: 51
<212> TYPE: DNA
<213> ORGANISM: Homo sapiens

<400> SEQUENCE: 100

```
gaaattaatc cagatagcag tacgataaac tatacgccat ctctaaggga t              51
```

<210> SEQ ID NO 101
<211> LENGTH: 21
<212> TYPE: DNA
<213> ORGANISM: Homo sapiens

<400> SEQUENCE: 101

```
gggagctact atccctctta c                                               21
```

<210> SEQ ID NO 102
<211> LENGTH: 45
<212> TYPE: DNA
<213> ORGANISM: Homo sapiens

<400> SEQUENCE: 102

```
agggccagca aaagtgtcag ttcatctggc tatagttata tgaac                     45
```

<210> SEQ ID NO 103
<211> LENGTH: 21
<212> TYPE: DNA
<213> ORGANISM: Homo sapiens

<400> SEQUENCE: 103

```
cttgcatcca acctagaatc t                                               21
```

<210> SEQ ID NO 104
<211> LENGTH: 27
<212> TYPE: DNA
<213> ORGANISM: Homo sapiens

<400> SEQUENCE: 104

```
cagcacagta gggagcttcc gcacacg                                         27
```

<210> SEQ ID NO 105
<211> LENGTH: 402
<212> TYPE: DNA
<213> ORGANISM: Homo sapiens

<400> SEQUENCE: 105

```
atggattttg ggctgatttt ttttattgtt gctcttttaa aagggtccaa gtgtgaagtg      60
aagcttctcg agtctggagg tggcctggtg cagcctggag atccctgaa actctcctgt      120
gcagcctcag gattcgattt tagtggatac tggatgactt gggtccggca ggctccaggg     180
aaagggctag aatggattgg agaaattaat ccagatagca gtacgataaa ctatacgcca     240
tctctaaggg ataaattcat catctccaga gacaacgcca gaatacgct gtacctgcaa      300
atgagcaaag tgagatctga ggacacagcc ctttatttct gtgcaagagg gagctactat     360
ccctcttact ggggccaagg gactctggtc actgtctctg ca                        402
```

<210> SEQ ID NO 106
<211> LENGTH: 393
<212> TYPE: DNA
<213> ORGANISM: Homo sapiens

<400> SEQUENCE: 106

```
atggagacag acacactcct gttatgggta ctgctgctct gggttccagg ttccactggg      60
gacattgtgc tgacacagtc tcctgcttcc ttagctgtat ctctgggca gagggccacc     120
atctcatgca gggccagcaa aagtgtcagt tcatctggct atagttatat gaactggtac     180
cagcagaaac caggacagcc acccaaactc ctcatctatc ttgcatccaa cctagaatct     240
ggggtccctg ccaggttcag tggcagtggg tctgggacag acttcaccct caacatccat     300
cctgtggagg atgaggatgc tgcaacctat tactgtcagc acagtaggga gcttccgcac     360
acgttcggag gggggaccaa gctggaaata aaa                                  393
```

<210> SEQ ID NO 107
<211> LENGTH: 18
<212> TYPE: DNA
<213> ORGANISM: Homo sapiens

<400> SEQUENCE: 107

```
agtggttatt actggaac                                                    18
```

<210> SEQ ID NO 108
<211> LENGTH: 48
<212> TYPE: DNA
<213> ORGANISM: Homo sapiens

<400> SEQUENCE: 108

```
tacataagct acgacggtaa caataactac aacccatctc tcaaaaat                   48
```

<210> SEQ ID NO 109
<211> LENGTH: 36
<212> TYPE: DNA
<213> ORGANISM: Homo sapiens

<400> SEQUENCE: 109

```
cctctctatg atggttatta ctggtacttc gatgtc                                36
```

<210> SEQ ID NO 110
<211> LENGTH: 33
<212> TYPE: DNA
<213> ORGANISM: Homo sapiens

<400> SEQUENCE: 110

```
ataaccagca ctgatattga tgatgatatg aac                                   33
```

<210> SEQ ID NO 111
<211> LENGTH: 21
<212> TYPE: DNA
<213> ORGANISM: Homo sapiens

<400> SEQUENCE: 111
gaagccaata ctcttcgtcc t                                              21

<210> SEQ ID NO 112
<211> LENGTH: 27
<212> TYPE: DNA
<213> ORGANISM: Homo sapiens

<400> SEQUENCE: 112
ttgcaaagtg ataacttgcc gtacacg                                        27

<210> SEQ ID NO 113
<211> LENGTH: 417
<212> TYPE: DNA
<213> ORGANISM: Homo sapiens

<400> SEQUENCE: 113
atgaaagtgt tgagtctgtt gtacctgttg acagccattc ctggtatcct gtctgatgta    60
cagcttcagg agtcaggacc tggcctcgtg aaaccttctc agtctctgtc tctcacctgc   120
tctgtcactg gctactccat caccagtggt tattactgga actggatccg gcagtttcca   180
ggaaacaaac tggaatggat gggctacata agctacgacg gtaacaataa ctacaaccca   240
tctctcaaaa atcgaatctc catcactcgt gacacgtcta agaaccagtt tttcctgaag   300
ttgaattctg tgactactga ggacacagct acatattact gtgcaagtcc tctctatgat   360
ggttattact ggtacttcga tgtctggggc gcagggacca cggtcaccgt ctcctca      417

<210> SEQ ID NO 114
<211> LENGTH: 387
<212> TYPE: DNA
<213> ORGANISM: Homo sapiens

<400> SEQUENCE: 114
atgaccatgt tctcactagc tcttctcctc agtcttcttc tcctctgtgt ctctgattct    60
agggcagaaa caactgtgac ccagtctcca gcatccctgt ccctggctat aggagaaaaa   120
gtcaccatca gatgcataac cagcactgat attgatgatg atatgaactg gtaccagcag   180
aagccagggg aacctcctaa gctccttatt tcagaagcca atactcttcg tcctggagtc   240
ccatcccgat tctccagcag tggccgtggt acagattttg tttttacaat tgaaaacatg   300
ctctcagaag atgttgcaga ttactactgt ttgcaaagtg ataacttgcc gtacacgttc   360 ggaggggga ccaagctgga aataaaa                                        387

ANTIBODIES HAVING SPECIFICITY FOR BTN2 AND USES THEREOF

FIELD OF THE INVENTION

The present invention relates to antibodies having specificity for BTN2 and uses thereof.

BACKGROUND

White blood cells are cells of the immune system involved in defending the body against pathogens. In addition to conventional MHC class I-restricted CD8+CTL and NK cells, other unconventional T cells, notably γδ T cells, display the same sensitivity and cytolytic power as NK and T cells. Vγ9/Vδ2 T cells are the main subset of circulating γδ T cells, representing 1-10% of human peripheral T cells.

Vγ9/Vδ2 T cells are important effectors of the immune defence. They lyse directly pathogen infected or abnormal cells. In addition, they regulate immune responses by inducing dendritic cell (DC) maturation as well as the isotypic switching and immunoglobulin production. This important cell platform of the immune system is strictly regulated by surface receptors, chemokines and cytokines. Vγ9/Vδ2 T cells are activated by nonpeptidic phosphorylated isoprenoid pathway metabolites, referred to as phosphoagonists (PAg).

The priming of T cells is modulated by involvement of specialised cells and secretion of chemotactic cytokines. Nowadays, we know that T-cell activation is the result of two synergistic events. The first is the interaction between the receptor of T cell (TCR) and the major histocompatibility complex (MHC) conjugated with processed antigen on the surface of the antigen presenting cells (APC). The second event is a co-stimulatory antigen-independent signal involving B7 molecules. The lack of co-stimulatory signal induces anergy, i.e. the inhibition of T cell proliferation, cytokine secretion and cytotoxic activities. The study of these pathways may provide insight about the triggering of pathologic events, such as autoimmune or lymphoproliferative disorders.

Butyrophilins constitute a family of transmembrane proteins comprising butyrophilin (BTN), BTN-like (BTNL), and selection and upkeep of intraepithelial T cell (SKINT) proteins (Arnett and Viney, 2014). Their extracellular moieties contain IgV and IgC2 domains exhibiting homology to the corresponding domains of B7 co-stimulatory molecules (Arnett and Viney, 2014), and butyrophilins are thus considered to be members of the extended B7 or Ig superfamily.

BTN1A1, the first butyrophilin identified, is required for the formation, secretion, and stabilization of milk fat globules (Ogg et al., 2004). Then, it has been proposed that B7 genes and MHC class I and II genes may have a common ancestral gene and could encode for proteins involved in similar function, such as T cell activation (Rhodes et al., 2001)

Growing evidence subsequently suggested that butyrophilins play diverse roles in the immune system. Functions have been best elucidated for mouse SKINT1 and human BTN3A1, which are not among the conserved family members. SKINT1 drives the thymic differentiation of mouse Vγ5+Vδ1+ T cells (Boyden et al., 2008).

BTN2 subfamily comprises BTN2A1, BTN2A2 and a pseudogene, BTN2A3 in humans. BTN2A1 and BTN2A2 protein isoforms display an IgV and an IgC extracellular domains, a transmembrane domain, and the characteristic intracellular domain B30.2, as for BTN3A1 and BTN3A3, but not BTN3A2. In mouse, BTN2A2 is a single copy gene and ortholog of the human BTN2A2 gene. Recombinant human BTN2A1-Fc protein revealed that a particular glycoform of BTN2A1 binds to a lectin molecule, DC-SIGN, found on dendritic cells (DCs). Binding of BTN2A1 to DC-SIGN is dependent on high-mannose glycosylation of the protein when expressed by tumor cells (Malcherek et al., 2007). To date, however, no clear function has been identified for human BTN2A1/A2 but some experiments have been performed in mice using recombinant Fc proteins.

Smith et al., 2010 showed that recombinant murine BTN2A2-Fc and BTN1A1-Fc bind to activated T cells, suggesting the presence of one or more receptors on these cells. Immobilized BTN2A2-Fc or BTN2A1-Fc proteins, but not MOG-Fc protein, inhibited the proliferation of CD4 and CD8 T cells activated by anti-CD3. Murine BTN1A1 and BTN2A2 also inhibited T cell metabolism, IL-2, and IFN-g secretion.

Amman et al., 2013 found that binding of mouse BTN2A2-Fc to CD3+ primary mouse T cells stimulated with anti-CD3 and anti-CD28 reduced the number of proliferating cells and entry of cells into the cell cycle. Binding of BTN2A2-Fc to anti-CD3− stimulated T cells inhibited CD3c, Zap70, and subsequent Erk1/2 activation. Murine BTN2A2-Fc also induce Foxp3 expression and Treg differentiation in vitro.

Sarter et al., 2016 showed that Btn2a2−/− mice exhibited enhanced effector CD4+ and CD8+ T cell responses, impaired CD4+ regulatory T cell induction, potentiated antitumor responses, and exacerbated experimental autoimmune encephalomyelitis.

To date, treatment of autoimmune diseases and prevention of transplantation rejection in graft versus host diseases (GVHD) depends on immunosuppressive agents that have serious side effects, or are not always effective. New immunosuppressive agents are therefore desired.

To date, the treatment of autoimmune diseases and the prevention of transplant rejection in graft versus host disease (GvHD) merely depend on immunosuppressive agents. However such immunosuppressive agents may not be always effective and/or have serious side effects.

There is therefore a need to identify new suppressive agents and/or methods to inhibit immune response in a patient in need thereof.

SUMMARY

The present disclosure relates to antibodies having specificity for BTN2 and uses thereof.

In particular, it is disclosed herein an antibody which binds to BTN2 (e.g. the human BTN2A1 and BTN2A2 polypeptides) and exhibiting at least one of the following properties:

it inhibits the production of IFN-γ and/or TNF-α by activated Vγ9/Vδ2 T cells, and/or it inhibits the cytolytic function of activated Vγ9/Vδ2 T cells, and/or it inhibits the proliferation of activated Vγ9/Vδ2 T cells In specific embodiments, the anti-BTN2 antibodies according to the present disclosure have specificity for both human butyrophilin-2A1 (BTN2A1) and human butyrophilin-2A2 (BTN2A2).

In specific embodiments, the anti-BTN2 antibodies according to the present disclosure compete for binding to BTN2A2 with at least one of the following reference murine antibodies:

i. mAb 4.15 as obtainable by the hybridoma deposited at the CNCM under deposit number CNCM 1-5231;

ii. mAb 5.28 as obtainable by the hybridoma deposited at the CNCM under deposit number CNCM 1-5232;
iii. mAb 7.28 as obtainable by the hybridoma deposited at the CNCM under deposit number CNCM 1-5233;
iv. mAb 7.48 as obtainable by the hybridoma deposited at the CNCM under deposit number CNCM 1-5234;
v. mAb 8.15 as obtainable by the hybridoma deposited at the CNCM under deposit number CNCM 1-5235; or
vi. mAb 8.16 as obtainable by the hybridoma deposited at the CNCM under deposit number CNCM 1-5236.

In specific embodiments, an anti-BTN2 antibody according to the present disclosure comprises either,
i. a heavy chain and a light chain comprising the 6 CDRs of the antibody mAb 4.15, said mAb 4.15 being obtainable by the hybridoma deposited at the CNCM under deposit number CNCM 1-5231;
ii. a heavy chain and a light chain comprising the 6 CDRs of the antibody mAb 5.28, said mAb 5.28 being obtainable by the hybridoma deposited at the CNCM under deposit number CNCM 1-5232;
iii. a heavy chain and a light chain comprising the 6 CDRs of the antibody mAb 7.28, said mAb 7.28 being obtainable by the hybridoma deposited at the CNCM under deposit number CNCM 1-5233;
iv. a heavy chain and a light chain comprising the 6 CDRs of the antibody mAb 7.48, said mAb 7.48 being obtainable by the hybridoma deposited at the CNCM under deposit number CNCM 1-5234;
v. a heavy chain and a light chain comprising the 6 CDRs of the antibody mAb 8.15, said mAb 8.15 being obtainable by the hybridoma deposited at the CNCM under deposit number CNCM 1-5235; or,
vi. a heavy chain and a light chain comprising the 6 CDRs of the antibody mAb 8.16, said mAb 8.16 being obtainable by the hybridoma deposited at the CNCM under deposit number CNCM 1-5236.

In other specific embodiments, the anti-BTN2 antibody of the present disclosure comprises either,
(i) the H-CDR1, H-CDR2, HCDR3, L-CDR1, L-CDR2 and L-CDR3 of the mAb 4.15 of SEQ ID NOs:3-8 respectively;
(ii) the H-CDR1, H-CDR2, HCDR3, L-CDR1, L-CDR2 and L-CDR3 of the mAb 5.28 of SEQ ID NOs:11-16 respectively;
(iii) the H-CDR1, H-CDR2, HCDR3, L-CDR1, L-CDR2 and L-CDR3 of the mAb 7.28 of SEQ ID NOs:19-24 respectively;
(iv) the H-CDR1, H-CDR2, HCDR3, L-CDR1, L-CDR2 and L-CDR3 of the mAb 7.48 of SEQ ID NOs:27-32 respectively; or,
(v) the H-CDR1, H-CDR2, HCDR3, L-CDR1, L-CDR2 and L-CDR3 of the mAb 8.15 of SEQ ID NOs:35-40 respectively
(vi) the H-CDR1, H-CDR2, HCDR3, L-CDR1, L-CDR2 and L-CDR3 of the mAb 8.16 of SEQ ID NOs:43-48 respectively.

In other specific embodiments, that may be combined with the previous embodiments, the anti-BTN2 antibody of the disclosure is an antibody comprising either,
(i) a heavy chain wherein the VH region has at least 95% identity with SEQ ID NO:9 and a light chain wherein the VL region has at least 95% identity with SEQ ID NO:10;
(ii) a heavy chain wherein the VH region has at least 95% identity with SEQ ID NO:17 and a light chain wherein the VL region has at least 95% identity with SEQ ID NO:18;
(iii) a heavy chain wherein the VH region has at least 95% identity with SEQ ID NO:25 and a light chain wherein the VL region has at least 95% identity with SEQ ID NO:26;
(iv) a heavy chain wherein the VH region has at least 95% identity with SEQ ID NO:33 and a light chain wherein the VL region has at least 95% identity with SEQ ID NO:34;
(v) a heavy chain wherein the VH region has at least 95% identity with SEQ ID NO:41 and a light chain wherein the VL region has at least 95% identity with SEQ ID NO:42; or,
(vi) a heavy chain wherein the VH region has at least 95% identity with SEQ ID NO:49 and a light chain wherein the VL region has at least 95% identity with SEQ ID NO:50.

In specific embodiments, the anti-BTN2 antibody according to the present disclosure does not cross-react with human CD277, in particular it does not cross-react with any one of human BTN3A1, BTN3A2 and BTN3A3.

In specific embodiments, the anti-BTN2 antibody according to the present disclosure inhibits the cytolytic function of activated Vγ9/Vδ2 T cells in the presence of the agonist anti-CD277 antibody mAb20.1.

In specific embodiments, the anti-BTN2 antibody according to the present disclosure inhibits the cytolytic function of activated Vγ9/Vδ2 T cells, for example as activated by co-culture with target cell line (ie Daudi cell line), and/or by phosphoagonists (PAg), and/or by agents that induce the production of phosphoagonists (PAg).

In specific embodiments, said anti-BTN2 antibody is a human, chimeric or humanized antibody.

Another aspect of the present disclosure relates to a nucleic acid molecule which encodes a heavy chain and/or a light chain of any of the anti-BTN2 antibodies as described above.

The disclosure also pertains to a host cell comprising such nucleic acids, in particular for use in the manufacturing of any one of the anti-BTN2 antibodies as described above.

Another aspect of the disclosure relates to the anti-BTN2 antibody as defined above, for use in therapy, for example in a method for treating autoimmune and inflammatory disorders and transplant rejection.

Another aspect of the disclosure relates to a method of treating autoimmune and inflammatory disorders and transplant rejection, in a subject in need thereof comprising administering to the subject, a therapeutically effective amount of the anti-BTN2 antibody as defined above.

Typically, said autoimmune and inflammatory disorders is selected among the group consisting of: rheumatoid arthritis (RA), insulin-dependent diabetes mellitus (Type 1 diabetes), multiple sclerosis (MS), Crohn's disease, systemic lupus erythematosus (SLE), scleroderma, Sjogren's syndrome, pemphigus vulgaris, pemphigoid, Addison's disease, ankylosing spondylitis, aplastic anemia, autoimmune hemolytic anemia, autoimmune hepatitis, coeliac disease, dermatomyositis, Goodpasture's syndrome, Graves' disease, Guillain-Barre syndrome, Hashimoto's disease, idiopathic leucopenia, idiopathic thrombocytopenic purpura, male infertility, mixed connective tissue disease, myasthenia gravis, pernicious anemia, phacogenic uveitis, primary biliary cirrhosis, primary myxoedema, Reiter's syndrome, stiff man syndrome, thyrotoxicosis, ulcerative colitis, and Wegener's granulomatosis.

The disclosure also relates to a pharmaceutical composition comprising the anti-BTN2 antibody as defined above.

The disclosure further provides a method for inhibiting an immune response in a subject, comprising administering to the subject an effective amount of an anti-BTN2 antibody as disclosed herein.

DETAILED DESCRIPTION OF THE INVENTION

Definitions

As used herein the term "BTN2" has its general meaning in the art and refers to human BTN2 polypeptides including either BTN2A1 of SEQ ID NO:1 or BTN2A2 of SEQ ID NO:2.

```
SEQ ID NO: 1: BTN2A isoform 1 precursor (Homo
sapiens):
MESAAALHFSRPASLLLLLLSLCALVSAQFIVVGPTDPILATVGENTTLR

CHLSPEKNAEDMEVRWFRSQFSPAVFVYKGGRERTEEQMEEYRGRTTFVS

KDISRGSVALVIHNITAQENGTYRCYFQEGRSYDEAILHLVVAGLGSKPL

ISMRGHEDGGIRLECISRGWYPKPLTVWRDPYGGVAPALKEVSMPDADGL

FMVTTAVIIRDKSVRNMSCSINNTLLGQKKESVIFIPESFMPSVSPCAVA

LPIIVVILMIPIAVCIYWINKLQKEKKILSGEKEFERETREIALKELEKE

RVQKEEELQVKEKLQEELRWRRTFLHAVDVVLDPDTAHPDLFLSEDRRSV

RRCPFRHLGESVPDNPERFDSQPCVLGRESEASGKHYWEVEVENVIEWTV

GVCRDSVERKGEVLLIPQNGFWTLEMHKGQYRAVSSPDRILPLKESLCRV

GVFLDYEAGDVSFYNMRDRSHIYTCPRSAFSVPVRPFFRLGCEDSPIFIC

PALTGANGVTVPEEGLTLHRVGTHQSL

SEQ ID NO: 2: BTN2A isofom 2 precursor (Homo
sapiens):
MEPAAALHFSLPASLLLLLLLLLSLCALVSAQFTVVGPANPILAMVGEN

TTLRCHLSPEKNAEDMEVRWFRSQFSPAVFVYKGGRERTEEQMEEYRGRI

TFVSKDINRGSVALVIHNVTAQENGIYRCYFQEGRSYDEAILRLVVAGLG

SKPLIEIKAQEDGSIWLECISGGWYPEPLTVWRDPYGEVVPALKEVSIAD

ADGLFMVTTAVIIRDKYVRNVSCSVNNTLLGQEKETVIFIPESFMPSASP

WMVALAVILTASPWMVSMTVILAVFIIFMAVSICCIKKLQREKKILSGEK

KVEQEEKEIAQQLQEELRWRRTFLHAADVVLDPDTAHPELFLSEDRRSVR

RGPYRQRVPDNPERFDSQPCVLGWESFASGKHYWEVEVENVMVWTVGVCR

HSVERKGEVLLIPQNGFWTLEMFGNQYRALSSPERILPLKESLCRVGVFL

DYEAGDVSFYNMRDRSHIYTCPRSAFTVPVRPFFRLGSDDSPIFICPALT

GASGVMVPEEGLKLHRVGTHQSL
```

As used herein the term "antibody" or "immunoglobulin" have the same meaning, and will be used equally in the present invention.

The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments.

In natural antibodies, two heavy chains are linked to each other by disulfide bonds and each heavy chain is linked to a light chain by a disulfide bond. There are two types of light chain, lambda (l) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR).

The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant Antibody combining sites are made up of residues that are primarily from the hypervariable or complementarity determining regions (CDRs). Occasionally, residues from nonhypervariable or framework regions (FR) can participate to the antibody binding site or influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDRs set from each of a heavy and a light chain V region. Framework Regions (FRs) refer to amino acid sequences interposed between CDRs. According the variable regions of the light and heavy chains typically comprise 4 framework regions and 3 CDRs of the following sequence: FR1-CDR1-FR2-CDR2-FR3-CDR3-FR4.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35 (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system.

In specific embodiments, an antibody provided herein is an antibody fragment, and more particularly any protein including an antigen-binding domain of an antibody as disclosed herein. Antibody fragments include, but are not limited to, Fv, Fab, F(ab')2, Fab', dsFv, scFv, sc(Fv)2 and diabodies.

As used herein, the term "specificity" refers to the ability of an antibody to detectably bind an epitope presented on an antigen, such as a BTN2. In some embodiments, it is intended to refer to an antibody or protein that binds to human BTN2A2 as expressed in a cell line, for example HEK293F cell lines as described in the examples, preferably with an EC50 below 50 µg/ml and more preferably below 10 µg/ml and even more preferably below 1 µg/ml as determined in the Examples and FIG. 1. In some embodiments, it is intended to refer to an antibody or protein that binds to human BTN2A1 as expressed in a cell line, for example HEK293F cell lines, which have been knocked-out for all isoforms of BTN3 and BTN2 as described in the examples, preferably with an EC50 below 1 µg/ml, for example below 0.1 µg/ml; and/or, it is intended to refer to an antibody or protein that binds to human BTN2A2 as expressed in a cell line, for example HEK293F cell lines which have been knocked-out for all isoforms of BTN3 and BTN2 as described in the examples, preferably with an EC50 below 50 µg/ml, for example below 1 µg/ml or below 0.02 µg/ml. In other embodiments, it binds to an antigen recombinant polypeptide with a $K_D$ of 100 nM or less, 10 nM or less, 1 nM or less, 100 pM or less, or 10 pM or less.

An antibody that "cross-reacts with an antigen other than BTN2" is intended to refer to an antibody that binds that antigen with a $K_D$ of 10 nM or less, 1 nM or less, or 100 pM or less. An antibody that "does not cross-react with a particular antigen" is intended to refer to an antibody that binds to that antigen, with a $K_D$ of 100 nM or greater, or a $K_D$ of 1 µM or grater, or a $K_D$ of 10 µM or greater. In certain embodiments, such antibodies that do not cross-react with the antigen exhibit essentially undetectable binding against these proteins in standard binding assays.

An "isolated antibody", as used herein, refers to an antibody that is substantially free of other antibodies having different antigenic specificities (e.g., an isolated antibody that specifically binds to BTN2 is substantially free of antibodies that specifically bind to other antigens than BTN2). An isolated antibody that specifically binds to BTN2 may, however, have cross-reactivity to other antigens, such as related BTN2 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The phrases "an antibody recognizing an antigen" and "an antibody having specificty for an antigen" are used interchangeably herein with the term "an antibody which binds specifically to an antigen".

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction.

The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. Preferred methods for determining the $K_D$ values of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. A method for determining the $K_D$ of an antibody is by using surface plasmon resonance, or using a biosensor system such as a Biacore® system.

Specificity can further be exhibited by, e.g., an about 10:1, about 20:1, about 50:1, about 100:1, 10.000:1 or greater ratio of affinity/avidity in binding to the specific antigen versus nonspecific binding to other irrelevant molecules (in this case the specific antigen is a BTN2 polypeptide). The term "affinity", as used herein, means the strength of the binding of an antibody to an epitope.

In one aspect, the present disclosure relates to an antibody having specificity for BTN2 characterized in that it has at least one of the following properties:

i. it inhibits the production of IFN-γ and TNF-α by activated Vγ9/Vδ2 T cells, and/or
ii. it inhibits the cytolytic function of activated Vγ9/Vδ2 T cells, and/or
iii. it inhibits the proliferation of activated Vγ9/Vδ2 T cells.

The anti-BTN2 antibodies of the present disclosure having such advantageous properties can be screened among anti-BTN2 antibodies using the cellular assays as described in the Examples and in particular the CD107 degranulation assay on Daudi cell lines.

As used herein, by "inhibiting the production of IFNγ or TNFα", it is meant that a significant decrease of the production of at least IFNγ or TNFα by activated Vγ9/Vδ2 T cells is observed when compared to control activated Vγ9/Vδ2 T cells (with IgG1 or IgG2a as control), said Vγ9/Vδ2 T cells being activated either by co-culture with target cell line (Daudi cell line) or by phosphoagonists (pAg). Typically, the inhibition of the production of IFNγ or TNFα by activated Vγ9/Vδ2 T cells may be measured in a cellular assay by intracellular labelling with antibodies against IFNγ or TNFα and flow cytometry. Such assay is described in more details in the examples below.

As used herein, by "inhibiting the cytolytic function of activated Vγ9/Vδ2 T cells", it is meant that a significant decrease of the cytolytic function of activated human Vγ9/Vδ2 T cells is observed when compared to control activated human Vγ9/Vδ2 T cells (with IgG1 or IgG2a as control), said human Vγ9/Vδ2 T cells being activated either by co-culture with target cell line (Daudi cell line) or phosphoagonists (pAg). Typically, the inhibition of the cytolytic function of activated Vγ9/Vδ2 T cells, for example in the presence of the agonist antibody mAb20.1, may be measured according to the measurement of the inhibition of the induction of γδ T cells degranulation against a standard cell line, and CD107 as degranulation marker for detecting positive degranulated γδ T cells. Such assay is described in more details in the examples below.

As used herein, by "inhibiting the proliferation of activated Vγ9/Vδ2 T cells", it is meant that a significant decrease of the proliferation of activated Vγ9/Vδ2 T cells is observed when compared to the proliferation with Vγ9/Vδ2 T cells activated with IgG1 or IgG2a as control, said Vγ9/Vδ2 T cells being activated either by co-culture with target cell line (Daudi cell line) or by phosphoagonists (pAg). Typically, the proliferation of activated Vγ9/Vδ2 T cells may be measured in a cellular assay by CFSE or Cell Trace violet staining and flow cytometry.

In some embodiments, the antibodies of the present invention inhibits the cytolytic function of activated Vγ9/Vδ2 T cells to a level that is substantially equal or superior to at least one of the reference antibodies: mAb 4.15, mAb 5.28, mAb 7.28, mAb 7.48, mAb 8.15, and mAb 8.16 as described below. In other specific embodiments, the anti-BTN2 antibodies inhibit the cytolytic function of activated Vγ9/VδT cells to a level at least equal or superior to mAb 103.2, said mAb 103.2 being disclosed in WO2012/080351.

In some embodiments, the antibodies of the present invention inhibits the production of at least IFNγ or TNFα by activated Vγ9/Vδ2 T cells to a level that is substantially equal or superior to at least one of the reference antibodies: mAb 4.15, mAb 5.28, mAb 7.28, mAb 7.48, mAb 8.15, and mAb 8.16 as described below. In other specific embodiments, the anti-BTN2 antibodies inhibit the cytolytic function of activated Vγ9/Vδ2 T cells to a level at least equal or superior to mAb 103.2, said mAb 103.2 being disclosed in WO2012/080351.

In specific embodiments, the anti-BTN2 antibodies according to the present disclosure are further characterized in that they inhibit the cytolytic function of activated Vγ9/Vδ2 T cells, even in the presence of an agonist anti-CD277 antibody mAb20.1.

The anti-CD277 antibody mAb 20.1 has been disclosed in WO2012/080351 and this antibody increases the cytolytic function of activated Vδ9/Vδ2 T cells. Typically, the inhibition of the cytolytic function of activated Vγ9/Vδ2 T cells in the presence of mAb20.1 may be measured according to the measurement of the inhibition of the induction of γδ T cells degranulation against a standard cell line, for example using the Daudi cell line as standard cell line, and CD107 as degranulation marker for detecting positive degranulated γδ T cells and using mAb 20.1 for example at a concentration of 10 µg/ml. Such assay is also described in more details in the examples below.

Reference Antibodies mAbs 1-6

Antibodies of the invention include the reference murine monoclonal antibodies mAb1-mAb6, as produced by the hybridomas which have been deposited at Collection Nationale de Cultures des Microorganismes (CNCM, Institut Pasteur, 25 rue du Docteur Roux, 75724 Paris Cedex 15, France), in accordance with the terms of the Budapest treaty on Sep. 14, 2017, under the respective deposit numbers as described in the Table 1 below:

TABLE 1 mAb1-mAb6

| Antibody | Clone Name | Deposit numbers |
| --- | --- | --- |
| mAb1 | 4.15 | CNCM I-5231 |
| mAb2 | 5.28 | CNCM I-5232 |
| mAb3 | 7.28 | CNCM I-5233 |
| mAb4 | 7.48 | CNCM I-5234 |
| mAb5 | 8.15 | CNCM I-5235 |
| mAb6 | 8.16 | CNCM I-5236 |

The invention further relates to any antibodies comprising the respective VH and VL regions of any one of the above reference antibodies.

The present invention further relates to the hybridomas accessible at the CNCM under deposit numbers CNCM 1-5231, CNCM 1-5232, CNCM 1-5233, CNCM 1-5234, CNCM 1-5235, or CNCM 1-5236.

Other antibodies of the invention include those having amino acids that have been mutated by amino acid deletion, insertion or substitution, yet have at least 60, 70, 80, 90, 95 or 100 percent identity in the CDR regions with the CDR regions of any one of the above reference antibodies.

In some embodiments, the antibody of the invention is a mutant variant of any one of mAb1-mAb6, having the 6 CDR regions 100% identical to the corresponding 6 CDR regions of one of reference mAb1-mAb6, and wherein said mutant variant antibody include mutant amino acid sequences wherein no more than 1, 2, 3, 4 or 5 amino acids have been mutated by amino acid deletion, insertion or substitution in the FR1, FR2, FR3 and FR4 regions when compared with the corresponding framework regions of the corresponding reference antibodies.

In particular embodiments, an anti-BTN2 antibody of the invention, preferably a humanized anti-BTN2, comprises either, i. a heavy chain and a light chain comprising the 6 CDRs of the antibody mAb 4.15, said mAb 4.15 being obtainable by the hybridoma deposited at the CNCM under deposit number CNCM 1-5231;

ii. a heavy chain and a light chain comprising the 6 CDRs of the antibody mAb 5.28, said mAb 5.28 being obtainable by the hybridoma deposited at the CNCM under deposit number CNCM 1-5232;

iii. a heavy chain and a light chain comprising the 6 CDRs of the antibody mAb 7.28, said mAb 7.28 being obtainable by the hybridoma deposited at the CNCM under deposit number CNCM 1-5233;

iv. a heavy chain and a light chain comprising the 6 CDRs of the antibody mAb 7.48, said mAb 7.48 being obtainable by the hybridoma deposited at the CNCM under deposit number CNCM 1-5234;

v. a heavy chain and a light chain comprising the 6 CDRs of the antibody mAb 8.15, said mAb 8.15 being obtainable by the hybridoma deposited at the CNCM under deposit number CNCM 1-5235; or, vi. a heavy chain and a light chain comprising the 6 CDRs of the antibody mAb 8.16, said mAb 8.16 being obtainable by the hybridoma deposited at the CNCM under deposit number CNCM 1-5236.

Antibodies of the disclosure thus also include the murine anti-BTN2 antibodies isolated and structurally characterized by their variable heavy and light chain amino acid sequences as described in the Table 2 below:

TABLE 2

Variable heavy and light chain amino acid sequences of murine reference antibodies of the disclosure

| Antibody | VH Amino acid sequence | VL Amino acid sequence |
| --- | --- | --- |
| mAb1 | SEQ ID NO: 9 | SEQ ID NO: 10 |
| mAb2 | SEQ ID NO: 17 | SEQ ID NO: 18 |
| mAb3 | SEQ ID NO: 25 | SEQ ID NO: 26 |
| mAb4 | SEQ ID NO: 33 | SEQ ID NO: 34 |
| mAb5 | SEQ ID NO: 41 | SEQ ID NO: 42 |
| mAb6 | SEQ ID NO: 49 | SEQ ID NO: 50 |

The corresponding amino acid and nucleotide coding sequence of the constant isotype regions of IgG4, IgG1 and their mutant versions are well-known in the art.

Examples of the amino acid sequences of the VH CDR1s (also called HCDR1), VH CDR2s (also called HCDR2), VH CDR3s (also called HCDR1), VL CDR1s (also called LCDR1), VL CDR2s (also called LCDR2), VL CDR3s (also called HCDR3) of some antibodies according to the disclosure are shown in Table 3.

In Table 3, the CDR regions of some antibodies of the present disclosure are delineated using the Chothia system (Chothia C, Lesk A M. 1987, J Mol Biol 196, 901-917).

For the ease of reading, the CDR regions are called hereafter HCDR1, HCDR2, HCDR3, LCDR1, LCDR2, LCDR3 respectively.

TABLE 3

CDR regions of reference murine antibodies according to Chothia definition

| Original antibody | HCDR1 | HCDR2 | HCDR3 | LCDR1 | LCDR2 | LCDR3 |
|---|---|---|---|---|---|---|
| mAb1 | SEQ ID NO: 3 | SEQ ID NO: 4 | SEQ ID NO: 5 | SEQ ID NO: 6 | SEQ ID NO: 7 | SEQ ID NO: 8 |
| mAb2 | SEQ ID NO: 11 | SEQ ID NO: 12 | SEQ ID NO: 13 | SEQ ID NO: 14 | SEQ ID NO :15 | SEQ ID NO: 16 |
| mAb3 | SEQ ID NO: 19 | SEQ ID NO: 20 | SEQ ID NO: 21 | SEQ ID NO: 22 | SEQ ID NO: 23 | SEQ ID NO: 24 |
| mAb4 | SEQ ID NO: 27 | SEQ ID NO: 28 | SEQ ID NO: 29 | SEQ ID NO: 30 | SEQ ID NO: 31 | SEQ ID NO: 32 |
| mAb5 | SEQ ID NO: 35 | SEQ ID NO: 36 | SEQ ID NO: 37 | SEQ ID NO: 38 | SEQ ID NO: 39 | SEQ ID NO: 40 |
| mAb6 | SEQ ID NO: 43 | SEQ ID NO: 44 | SEQ ID NO: 45 | SEQ ID NO: 46 | SEQ ID NO: 47 | SEQ ID NO: 48 |

In specific embodiments, the isolated anti-BTN2 antibody according to the disclosure comprises either:

(a) a variable heavy chain polypeptide comprising HCDR1 of SEQ ID NO:3, HCDR2 of SEQ ID NO:4, HCDR3 of SEQ ID NO:5 and a variable light chain polypeptide comprising LCDR1 of SEQ ID NO:6, LCDR2 of SEQ ID NO:7 and LCDR3 of SEQ ID NO:8;

(b) a variable heavy chain polypeptide comprising HCDR1 of SEQ ID NO:11, HCDR2 of SEQ ID NO:12, HCDR3 of SEQ ID NO:13 and a variable light chain polypeptide comprising LCDR1 of SEQ ID NO:14, LCDR2 of SEQ ID NO:15 and LCDR3 of SEQ ID NO:16;

(c) a variable heavy chain polypeptide comprising HCDR1 of SEQ ID NO:19, HCDR2 of SEQ ID NO:20, HCDR3 of SEQ ID NO:21 and a variable light chain polypeptide comprising LCDR1 of SEQ ID NO:22, LCDR2 of SEQ ID NO:23 and LCDR3 of SEQ ID NO:24;

(d) a variable heavy chain polypeptide comprising HCDR1 of SEQ ID NO:27, HCDR2 of SEQ ID NO:28, HCDR3 of SEQ ID NO:29 and a variable light chain polypeptide comprising LCDR1 of SEQ ID NO:30, LCDR2 of SEQ ID NO:31 and LCDR3 of SEQ ID NO:32;

(e) a variable heavy chain polypeptide comprising HCDR1 of SEQ ID NO:35, HCDR2 of SEQ ID NO:36, HCDR3 of SEQ ID NO:37 and a variable light chain polypeptide comprising LCDR1 of SEQ ID NO:38, LCDR2 of SEQ ID NO:39 and LCDR3 of SEQ ID NO:40; or (f) a variable heavy chain polypeptide comprising HCDR1 of SEQ ID NO:43, HCDR2 of SEQ ID NO:44, HCDR3 of SEQ ID NO:45 and a variable light chain polypeptide comprising LCDR1 of SEQ ID NO:46, LCDR2 of SEQ ID NO:47 and LCDR3 of SEQ ID NO:48.

wherein said anti-BTN2 antibody has specificity for BTN2.

In other specific embodiments, the isolated anti-BTN2 antibody according to the disclosure comprises either:

(a) a variable heavy chain polypeptide comprising VH of SEQ ID NO:9 and a variable light chain polypeptide VL of SEQ ID NO:10;

(b) a variable heavy chain polypeptide comprising VH of SEQ ID NO:17 and a variable light chain polypeptide VL of SEQ ID NO:18;

(c) a variable heavy chain polypeptide comprising VH of SEQ ID NO:25 and a variable light chain polypeptide VL of SEQ ID NO:26;

(d) a variable heavy chain polypeptide comprising VH of SEQ ID NO:33 and a variable light chain polypeptide VL of SEQ ID NO:34;

(e) a variable heavy chain polypeptide comprising VH of SEQ ID NO:41 and a variable light chain polypeptide VL of SEQ ID NO:42;

(f) a variable heavy chain polypeptide comprising VH of SEQ ID NO:49 and a variable light chain polypeptide VL of SEQ ID NO:50; or, wherein said anti-BTN2 antibody has specificity for BTN2.

Functional Variant Antibodies

In yet another embodiment, a functional variant antibody of the invention has full length heavy and light chain amino acid sequences; or variable region heavy and light chain amino acid sequences, or all 6 CDR regions amino acid sequences that are homologous or preferably identical to the corresponding amino acid sequences of the antibodies mAb1-mAb6 described above, in particular in Tables 1, 2 and 3, and wherein such functional variant antibodies retain the desired functional properties of the original mAb 1-mAb6 antibodies.

A functional variant of a VL, VH, or CDR used in the context of a monoclonal antibody of the present invention still allows the antibody to retain at least a substantial proportion (at least about 50%, 60%, 70%, 80%, 90%, 95% or 100%) of the affinity/avidity and/or the specificity/selectivity of the parent antibody (i.e. any one of mAb 1-mAb6 antibody) and in some cases such a monoclonal antibody of the present invention may be associated with greater affinity, selectivity and/or specificity than the parent Ab.

Desired functional properties of the original mAb1-mAb6 antibodies may be selected from the group consisting of:

i. it has specificity for BTN2, in particular it binds to human BTN2 as expressed in a cell line, for example HEK293F cell lines expressing human BTN2A2, as described in the examples, preferably with an $EC_{50}$ below 50 µg/ml and more preferably below 10 µg/ml and even more preferably below 1 µg/ml as determined in the Examples and FIG. 1, ii. it binds to human BTN2A1 as expressed in a cell line, for example HEK293F cell lines, which have been knocked-out for all isoforms of BTN3 and BTN2 as described in the examples, preferably with an EC50 below 1 µg/ml, for example below 0.1 µg/ml, iii. it binds to human BTN2A2 as expressed in a cell line, for example HEK293F cell lines which have been knocked-out for all isoforms of BTN3 and BTN2 as described in the examples, preferably with an EC50 below 50 µg/ml, for example below 1 µg/ml or below 0.02 µg/ml, iv. it inhibits production of IFNγ or TNFα of activated Vγ9/Vδ2 T cells, v. it inhibits the cytolytic function of activated Vγ9/Vδ2 T cells, and/or vi. it inhibits the proliferation of activated Vγ9/Vδ2 T cells.

For example, the invention relates to functional variant antibodies of mAb1-mAb6, comprising a variable heavy chain ($V_H$) and a variable light chain (VL) sequences where the CDR sequences, i.e. the 6 CDR regions; HCDR1, HCDR2, HCDR3, LCDR1, LCDR2, LCDR3 share at least 60, 70, 90, 95 or 100 percent sequence identity to the corresponding CDR sequences of at least one antibody of mAb1-mAb6, wherein said functional variant antibody specifically binds to BTN2, and the antibody exhibits at least one of the following functional properties:

i. it inhibits production of IFNγ or TNFα of activated Vγ9/Vδ2 T cells, ii. it inhibits the cytolytic function of activated Vγ9/Vδ2 T cells, and/or, iii. it inhibits the proliferation of activated Vγ9/Vδ2 T cells.

It further relates to functional variant antibodies of mAb1-mAb6 comprising a heavy chain variable region and a light chain variable region that are at least 80%, 90%, or at least 95% or 100% identical to the corresponding heavy and light chain variable regions of any one of mAb1-mAb6 antibodies, as shown in particular in Table 2; the functional variant antibody specifically binds to BTN2, and exhibits at least one of the following functional properties:

i. it inhibits production of IFNγ or TNFα of activated Vγ9/Vδ2 T cells, ii. it inhibits the cytolytic function of activated Vγ9/Vδ2 T cells, and/or iii. it inhibits the proliferation of activated Vγ9/Vδ2 T cells.

In various embodiments, the antibody may exhibit one or two of the desired functional properties discussed above. The antibody can be, for example, a human antibody, a humanized antibody or a chimeric antibody. Preferably the antibody or protein is a humanized human antibody, more preferably a humanized silent antibody.

As used herein, the term "silent" antibody refers to an antibody that exhibits no or low ADCC activity as measured in an in vitro ADCC activity assay measuring cell lysis of target cells.

In one embodiment, the term "no or low ADCC activity" means that the silent antibody exhibit an ADCC activity that is at below 50%, for example below 10% of the ADCC activity that is observed with the corresponding wild type (non silent) antibody for example with a wild type human IgG1 antibody. Preferably, no detectable ADCC activity is observed in an in vitro ADCC activity assay with a silent antibody as compared to a control Fab antibody.

Silenced effector functions can be obtained by mutation in the Fc constant part of the antibodies and have been described in the Art: Strohl 2009 (LALA & N297A); Baudino 2008, D265A (Baudino et al., J. Immunol. 181 (2008): 6664-69, Strohl, CO Biotechnology 20 (2009): 685-91). Examples of silent IgG1 antibodies comprise mutations reducing ADCC at positions 234, 235 and/or 331 in the IgG1 Fc amino acid sequence (EU numbering). Another silent IgG1 antibody comprises the N297A mutation, which results in aglycosylated or non-glycosylated antibodies.

The sequences of CDR variants may differ from the sequence of the CDRs of the parent antibody sequences (as shown for example in Table 3) through mostly conservative substitutions; for instance at least 10, such as at least 9, 8, 7, 6, 5, 4, 3, 2 or 1 of the substitutions in the variant are conservative amino acid residue replacements. In the context of the present invention, conservative substitutions may be defined by substitutions within the classes of amino acids reflected as follows:

Aliphatic residues I, L, V, and M
Cycloalkenyl-associated residues F, H, W, and Y
Hydrophobic residues A, C, F, G, H, I, L, M, R, T, V, W, and Y
Negatively charged residues D and E
Polar residues C, D, E, H, K, N, Q, R, S, and T
Positively charged residues H, K, and R
Small residues A, C, D, G, N, P, S, T, and V
Very small residues A, G, and S
Residues involved in turn A, C, D, E, G, H, K, N, Q, R, S, P, and formation T
Flexible residues Q, T, K, S, G, P, D, E, and R More conservative substitutions groupings include: valine-leucine-isoleucine, phenylalanine-tyrosine, lysine-arginine, alanine-valine, and asparagine-glutamine Conservation in terms of hydropathic/hydrophilic properties and residue weight/size also is substantially retained in a variant CDR as compared to a CDR of the any one of mAbs 1-6. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The retention of similar residues may also or alternatively be measured by a similarity score, as determined by use of a BLAST program (e.g., BLAST 2.2.8 available through the NCBI using standard settings BLOSUM62, Open Gap=1 1 and Extended Gap=1). Suitable variants typically exhibit at least about 70% of identity to the parent peptide. According to the present invention a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100% of identity with the second amino acid sequence. According to the present invention a first amino acid sequence having at least 50% of identity with a second amino acid sequence means that the first sequence has 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100% of identity with the second amino acid sequence.

In some embodiments, the antibody of the present invention is a chimeric antibody, typically a chimeric mouse/ human antibody. The term "chimeric antibody" refers to a monoclonal antibody which comprises a VH domain and a VL domain of an antibody derived from a non-human animal, a CH domain and a CL domain of a human antibody. As the non-human animal, any animal such as mouse, rat, hamster, rabbit or the like can be used. In particular, said mouse/human chimeric antibody may comprise the VH and the VL domains of any one of mAb1-mAb6 reference antibodies.

In some embodiments, the antibody of the present invention is a humanized antibody. In specific embodiments, the antibody of the present invention is a humanized antibody which comprises the 6 CDRs of any one of the mAb1-mAb6 reference antibodies, for example as shown in Table 3. As used herein the term "humanized antibody" refers to antibodies in which the framework regions (FRs) have been modified to comprise the FRs from a donor immunoglobulin of different species (for example human species) as compared to that of the parent immunoglobulin (for example murine CDRs).

In some embodiments, the antibody of the present invention is selected from the group consisting of Fab, F(ab')2, Fab' and scFv. As used herein, the term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond. The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin. The term "Fab'" refers to an antibody fragment having a molecular weight of about 50,000 and antigen binding activity, which is obtained by cutting a disulfide bond of the hinge region of the F(ab')2. A single chain Fv ("scFv") polypeptide is a covalently linked VH:: VL heterodimer which is usually expressed from a gene fusion including VH and VL encoding genes linked by a peptide-encoding linker. The human scFv fragment of the invention includes CDRs that are held in appropriate conformation, preferably by using gene recombination techniques.

Functional variant antibodies with mutant amino acid sequences can be obtained by mutagenesis (e.g., site-directed or PCR-mediated mutagenesis) of the coding nucleic acid molecules, followed by testing of the encoded altered antibody for retained function (i. e., the functions set forth above) using the functional assays described herein.

Antibodies that Cross-Block any One of mAb1-mAb6 and/ or that Bind to the Same Epitope as mAb1-mAb6

Additional antibodies with similar advantageous properties of the reference antibodies mAb1-mAb6 as disclosed herein can be identified based on their ability to cross-compete (e.g., to competitively inhibit the binding of), in a statistically significant manner with any one of the reference antibodies mAb1-mAb6 as described above, in standard BTN2 binding assays.

Test antibody may first be screened for their binding affinity to BTN2, for example from human recombinant antibody libraries using for example phage display technologies or from transgenic mouse expressing human variable region antibodies immunized with BTN2 antigens.

The ability of a test antibody to cross-compete with or inhibit the binding of antibodies of the present invention to human BTN2 demonstrates that the test antibody can compete with that antibody for binding to human BTN2; such an antibody may, according to non-limiting theory, bind to the same or a related (e.g., a structurally similar or spatially proximal) epitope on human BTN2 (e.g. BTN2A2 and/or BTN2A1) as the antibody with which it competes.

To screen an anti-BTN2 antibody for its ability to binds to the same epitope as one of mAb1-mAb6 reference antibodies, for example, HEK293 cells transfected with human BTN2A2 or HEK293 cells knocked-out for all isoforms of BTN2 or BTN3 and expressing human BTN2A2 or human BTN2A1 (as described in the examples) are stained with saturing concentration (10 µg/ml) of one of the reference antibodies mAb1-mAb6 during 30 minutes at 4° C. After 2 washes, different doses of a test anti-BTN2 mAbs are tested (30 min at 4° C.) for their competitive potential with any one of mAb1-mAb6 reference antibodies. The mAbs that do compete for the same binding site as the reference antibody will not be able to recognize BTN2 in the presence of such reference antibodies. The data can be expressed as mean fluorescence intensity.

The selected antibodies can be further tested for the advantageous properties of mAb1-mAb6 in particular with respect to inhibition properties against activated Vγ9/Vδ2 T cells.

Accordingly, in one embodiment, the invention provides an isolated antibody which cross-blocks or is cross-blocked by at least one antibody of mAb1-mAb6, from binding to BTN2, wherein said antibody:
  i. has specificity to BTN2, in particular it binds to human BTN2 as expressed in a cell line, for example HEK293F cell lines expressing human BTN2A2, as described in the examples, preferably with an EC50 below 50 µg/ml and more preferably below 10 µg/ml and even more preferably below 1 µg/ml as determined in the Examples and FIG. 1,
  ii. it binds to human BTN2A1 as expressed in a cell line, for example HEK293F cell lines, which have been knocked-out for all isoforms of BTN3 and BTN2 as described in the examples, preferably with an EC50 below 1 µg/ml, for example below 0.1 µg/ml,
  iii. it binds to human BTN2A2 as expressed in a cell line, for example HEK293F cell lines which have been knocked-out for all isoforms of BTN3 and BTN2 as described in the examples, preferably with an EC50 below 50 µg/ml, for example below 1 µg/ml or below 0.02 µg/ml,
  iv. it inhibits production of IFNγ and/or TNFα by activated Vγ9Vδ2 T cells,
  v. it inhibits the cytolytic function of activated Vγ9Vδ2 T cells, and/or
  vi. it inhibits the proliferation of activated Vγ9/Vδ2 T cells.

In another embodiment, the invention provides antibodies that bind to the same epitope as do at least one of the anti-BTN2 antibodies mAb1-mAb6 as described herein.

In a certain embodiment, the cross-blocking antibodies or antibody that binds to the same epitope on human BTN2 as any one of mAb1-mAb6, is a chimeric, humanized or human recombinant antibody.

Generation of Transfectomas Producing Monoclonal Antibodies

The antibodies of the present invention are produced by any techniques known in the art, such as, without limitation, any chemical, biological, genetic or enzymatic technique, either alone or in combination. Typically, knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the present invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Accordingly, a further object of the invention relates to a nucleic acid molecule encoding an antibody according to the invention. More particularly the nucleic acid molecule encodes a heavy chain or a light chain of an antibody of the present invention. More particularly the nucleic acid molecule comprises a VH or VL coding region having at least 70%, 80%, 90%, 95% or 100% of identity to the corresponding nucleic acid encoding heavy chain variable region (VH region) or light chain variable region (VL) of any one of the reference antibodies mAb1-mAb6.

Typically, said nucleic acid is a DNA or RNA molecule, which may be included in any suitable vector, such as a plasmid, cosmid, episome, artificial chromosome, phage or a viral vector. As used herein, the terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. So, a further object of the invention relates to a vector comprising a nucleic acid of the invention. Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40, LTR promoter and enhancer of Moloney mouse leukemia virus, promoter and enhancer of immunoglobulin H chain and the like. Any expression vector for animal cell can be used, so long as a gene encoding the human antibody C region can be inserted and expressed. Examples of suitable vectors include pAGE107, pAGE103, pHSG274, pKCR, pSG1 beta d2-4 and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further object of the present invention relates to a host cell which has been transfected, infected or transformed by a nucleic acid and/or a vector as described above. As used herein, the term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

The nucleic acids of the invention may be used to produce an antibody of the present invention in a suitable expression system. The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like.

The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the present invention.

Antibodies of the present invention are suitably separated from the culture medium by conventional immunoglobulin purification procedures such as, for example, protein A-Sepharose®, hydroxylapatite chromatography, gel electrophoresis, dialysis, or affinity chromatography.

In some embodiments, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used. Methods for producing chimeric antibodies involve conventional recombinant DNA and gene transfection techniques are well known in the art (See Morrison S L. et al. (1984) and patent documents U.S. Pat. Nos. 5,202,238; and 5,204,244).

The humanized antibody of the present invention may be produced by obtaining nucleic acid sequences encoding CDR domains, as previously described, constructing a humanized antibody expression vector by inserting them into an expression vector having genes encoding (i) a heavy chain constant region and heavy chain variable framework regions identical to that of a human antibody and (ii) a light chain constant region and light chain variable framework regions identical to that of a human antibody, and expressing the genes by introducing the expression vector into suitable cell line. The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into cell lines, and balance between the expression levels of antibody H and L chains in cell lines, humanized antibody expression vector of the tandem type is preferred. Examples of tandem type humanized antibody expression vector include pKANTEX93 (WO 97/10354), pEE18 and the like.

Methods for humanizing antibodies based on conventional recombinant DNA and gene transfection techniques are well known in the art (See, e. g., Riechmann L et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530, 101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts with AMH with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present invention can be obtained treating an antibody which specifically reacts with AMH with a protease, pepsin. Also, the F(ab')2 can be produced by binding Fab' described below via a thioether bond or a disulfide bond.

The Fab' of the present invention can be obtained treating F(ab')2 which specifically reacts with AMH with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv.

To generate a humanized scFv fragment, the well-known technology called CDR grafting may be used, which involves selecting the complementary determining regions (CDRs) from a donor scFv fragment, and grafting them onto a human scFv fragment framework of known three dimensional structure (see, e. g., WO98/45322; WO 87/02671; U.S. Pat. Nos. 5,859,205; 5,585,089; 4,816,567; EP0173494).

Engineered antibodies of the present invention further include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention. Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

Fc Engineering

The antibody of the invention can be characterized by one or more of the functional or structural features of the aspects described above, or by any combination of selected functional and structural features.

The antibody of the invention may be of any isotype. The choice of isotype typically will be guided by the desired effector functions, such as ADCC silencing. Exemplary isotypes are IgG1, IgG2, IgG3, and IgG4. Either of the human light chain constant regions, kappa or lambda, may be used. If desired, the class of an antibody of the present invention may be switched by known methods. Typical, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses. In some embodiments, the antibody of the invention is a full-length antibody. In some embodiments, the full-length antibody is an IgG1 antibody. In some embodiments, the full-length antibody is an IgG4 antibody. In some embodiments, the BTN2-specific IgG4 antibody is a stabilized IgG4 antibody. Examples of suitable stabilized IgG4 antibodies are antibodies wherein arginine at position 409 in a heavy chain constant region of human IgG4, which is indicated in the EU index as in Kabat et al. supra, is substituted with lysine, threonine, methionine, or leucine, preferably lysine (described in WO2006033386) and/or wherein the hinge region comprises a Cys-Pro-Pro-Cys sequence. Other suitable stabilized IgG4 antibodies are disclosed in WO2008145142.

In some embodiments, the antibody of the present invention does not comprise a Fc portion that induces antibody dependent cellular cytotoxicity (ADCC). The terms "Fc domain," "Fc portion," and "Fc region" refer to a C-terminal fragment of an antibody heavy chain, e.g., from about amino acid (aa) 230 to about aa 450 of human gamma heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md.). In some embodiments, the antibody of the present invention does not comprise an Fc domain capable of substantially binding to a FcgRIIIA (CD16) polypeptide. In some embodiments, the antibody of the present invention lacks an Fc domain (e.g. lacks a CH2 and/or CH3 domain) or comprises an Fc domain of IgG2 or IgG4 isotype. In some embodiments, the antibody of the present invention consists of or comprises a Fab, Fab', Fab'-SH, F (ab') 2, Fv, a diabody, single-chain antibody fragment, or a multispecific antibody comprising multiple different antibody fragments. In some embodiments, the antibody of the present invention is not linked to a toxic moiety. In some embodiments, one or more amino acids selected from amino acid residues can be replaced with a different amino acid residue such that the antibody has altered C2q binding and/or reduced or abolished complement dependent cytotoxicity (CDC). This approach is described in further detail in U.S. Pat. No. 6,194,551.

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (CI-CIO) alkoxy- or aryloxy-poly ethylene glycol or polyethylene glycol-maleimide. In some embodiments, the antibody to be pegylated is an aglycosylated antibody. Methods for pegylating proteins are known in the art and can be applied to the antibodies of the present invention. See for example, EP 0154 316 by Nishimura et al. and EP 0 401 384 by Ishikawa et al.

Another modification of the antibodies that is contemplated by the invention is a conjugate or a protein fusion of at least the antigen-binding region of the antibody of the present invention to serum protein, such as human serum albumin or a fragment thereof to increase half-life of the resulting molecule.

In some embodiments, the invention also provides a multispecific antibody. Exemplary formats for the multispecific antibody molecules of the invention include, but are not limited to (i) two antibodies cross-linked by chemical heteroconjugation, one with a specificity to BTN2 and another with a specificity to a second antigen; (ii) a single antibody that comprises two different antigen-binding regions; (iii) a single-chain antibody that comprises two different antigen-binding regions, e.g., two scFvs linked in tandem by an extra peptide linker; (iv) a dual-variable-domain antibody (DVD-Ig™), where each light chain and heavy chain contains two variable domains in tandem through a short peptide linkage (Wu et al., Generation and Characterization of a Dual Variable Domain Immunoglobulin (DVD-Ig™) Molecule, in: Antibody Engineering, Springer Berlin Heidelberg (2010)); (v) a chemically-linked bispecific (Fab')2 fragment; (vi) a TandAb, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (ix) a so-called Scorpion molecule, comprising, e.g., two scFvs fused to both termini of a human Fab-arm; and (x) a diabody. Another exemplary format for bispecific antibodies is IgG-like molecules with complementary CH3 domains to force heterodimerization. Such molecules can be prepared using known technologies, such as, e.g., those known as Triomab®/Quadroma (Trion Pharma/Fresenius Biotech), Knob-into-Hole (Genentech), CrossMAb (Roche) and electrostatically-matched (Amgen), LUZ-Y (Genentech), Strand Exchange Engineered Domain body (SEEDbody) (EMD Serono), Biclonics® (Merus) and DuoBody® (Genmab A/S) technologies. In some embodiments, the bispecific antibody is obtained or obtainable via a controlled Fab-arm exchange, typically using DuoBody® technology. In vitro methods for producing bispecific antibodies by controlled Fab-arm exchange have been described in WO2008119353 and WO 2011131746 (both by Genmab A/S). In one exemplary method, described in WO 2008119353, a bispecific antibody is formed by "Fab-arm" or "half-molecule" exchange (swapping of a heavy chain and attached light chain) between two monospecific antibodies, both comprising IgG4-like CH3 regions, upon incubation under reducing conditions. The resulting product is a bispecific antibody having two Fab: arms which may comprise different sequences. In another exemplary method, described in WO 2011131746, bispecific antibodies of the present invention are prepared by a method comprising the following steps, wherein at least one of the first and second antibodies is the antibody of the present invention: a) providing a first antibody comprising an Fc region of an immunoglobulin, said Fc region comprising a first CH3 region; b) providing a second antibody comprising an Fc region of an immunoglobulin, said Fc region comprising a second CH3 region; wherein the sequences of said first and second CH3 regions are different and are such that the heterodimeric interaction between said first and second CH3 regions is stronger than each of the homodimeric interactions of said first and second CH3 regions; c) incubating said first antibody together with said second antibody under reducing conditions; and d) obtaining said bispecific antibody, wherein the first antibody is the antibody of the present invention and the second antibody has a different binding specificity, or vice versa. The reducing conditions may, for example, be provided by adding a reducing agent, e.g. selected from 2-mercaptoethylamine, dithiothreitol and tris(2-carboxyethyl)phosphine. Step d) may further comprise restoring the conditions to become non-reducing or less reducing, for example by removal of a reducing agent, e.g. by desalting. Preferably, the sequences of the first and second CH3 regions are different, comprising only a few, fairly conservative, asymmetrical mutations, such that the heterodimeric interaction between said first and second CH3 regions is stronger than each of the homodimeric interactions of said first and second CH3 regions. More details on these interactions and how they can be achieved are provided in WO 2011131746, which is hereby incorporated by reference in its entirety. The following are exemplary embodiments of combinations of such asymmetrical mutations, optionally wherein one or both Fc-regions are of the IgG1 isotype.

Uses and Methods of the Invention

The antibodies or proteins of the present invention have in vitro and in vivo diagnostic and therapeutic utilities. For example, these molecules can be administered to cells in culture, e.g. in vitro or in vivo, or in a subject, e.g., in vivo, to treat, prevent or diagnose a variety of disorders.

The methods are particularly suitable for treating, preventing or diagnosing BTN2-related disorders and/or autoimmune, inflammatory disorders, and transplant rejection.

The disclosure also pertains to the methods of manufacturing a medicament for use in the treatment of inflammatory conditions, autoimmune diseases and organ or tissue transplant rejection, said medicament comprising an anti-BTN2 antibody of the present disclosure as described in the previous sections.

As used herein, a "BTN2-related disorder" includes conditions associated with or characterized by aberrant BTN2A1 or BTN2A2 levels and/or diseases or conditions that can be treated by modulating BTN2A1 and/or BTN2A2 induced signaling activity in human blood cells e.g. by inhibiting the production of IFNγ or TNFα of activated Vγ9Vδ2 T cells and/or the cytolytic function of activated Vγ9Vδ2 T cells. These include inflammatory conditions, autoimmune diseases and organ or tissue transplant rejection. Examples of autoimmune diseases which may be treated include but are not limited to rheumatoid arthritis (RA), insulin-dependent diabetes mellitus (Type 1 diabetes), multiple sclerosis (MS), Crohn's disease, systemic lupus erythematosus (SLE), scleroderma, Sjogren's syndrome, pemphigus vulgaris, pemphigoid, Addison's disease, ankylosing spondylitis, aplastic anemia, autoimmune hemolytic anemia, autoimmune hepatitis, coeliac disease, dermatomyositis, Goodpasture's syndrome, Graves' disease, Guillain-Barre syndrome, Hashimoto's disease, idiopathic leucopenia, idiopathic thrombocytopenic purpura, male infertility, mixed connective tissue disease, myasthenia gravis, pernicious anemia, phacogenic uveitis, primary biliary cirrhosis, primary myxoedema, Reiter's syndrome, stiff man syndrome, thyrotoxicosis, ulcerative colitis, and Wegener's granulomatosis.

The antibodies of the invention may be administered as the sole active ingredient or in conjunction with, e.g. as an adjuvant to or in combination to, other drugs e.g. immunosuppressive or immunomodulating agents or other anti-inflammatory agents, e.g. for the treatment or prevention of diseases mentioned above.

An object of the present invention relates to a method of inhibiting an immune response in a subject, in particular inhibiting the cytolytic property of Vγ9Vδ2 T cells in a subject in need thereof, comprising administering to the subject a therapeutically effective amount of an antibody of the present invention.

As used herein, the term "treatment" or "treat" refer to both prophylactic or preventive treatment as well as curative or disease modifying treatment, including treatment of subject at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "therapeutically effective amount" refers to an amount effective, at dosages and for periods of time necessary, to achieve a desired therapeutic result. A therapeutically effective amount of the antibody of the present invention may vary according to factors such as the disease state, age, sex, and weight of the individual, and the ability of the antibody of the present invention to elicit a desired response in the individual. A therapeutically effective amount is also one in which any toxic or detrimental effects of the antibody or antibody portion are outweighed by the therapeutically beneficial effects. The efficient dosages and dosage regimens for the antibody of the present invention depend on the disease or condition to be treated and may be determined by the persons skilled in the art. A physician having ordinary skill in the art may readily determine and prescribe the effective amount of the pharmaceutical composition required. For example, the physician could start doses of the antibody of the present invention employed in the pharmaceutical composition at levels lower than that required in order to achieve the desired therapeutic effect and gradually increase the dosage until the desired effect is achieved. In general, a suitable dose of a composition of the present invention will be that amount of the compound which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. Typically, the ability of a compound to treat autoimmune disorders, for example, be evaluated in an animal model system predictive of efficacy in treating autoimmune disorders. Alternatively, this property of a composition may be evaluated by examining the ability of the compound to inhibit induction of immune response by in vitro assays known to the skilled practitioner. A therapeutically effective amount of a therapeutic compound may decrease immune or inflammatory response, or otherwise ameliorate symptoms in a subject. One of ordinary skill in the art would be able to determine such amounts based on such factors as the subject's size, the severity of the subject's symptoms, and the particular composition or route of administration selected. An exemplary, non-limiting range for a therapeutically effective amount of an antibody of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg. An exemplary, non-limiting range for a therapeutically effective amount of an antibody of the present invention is 0.02-100 mg/kg, such as about 0.02-30 mg/kg, such as about 0.05-10 mg/kg or 0.1-3 mg/kg, for example about 0.5-2 mg/kg. Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. In some embodiments, the efficacy of the treatment is monitored during the therapy, e.g. at pre-defined points in time. In some embodiments, the efficacy may be monitored by visualization of the disease area, or by other diagnostic methods described further herein, e.g. by performing one or more PET-CT scans, for example using a labeled antibody of the present invention, fragment or mini-antibody derived from the antibody of the present invention. If desired, an effective daily dose of a pharmaceutical composition may be administered as two, three, four, five, six or more sub-doses administered separately at appropriate intervals throughout the day, optionally, in unit dosage forms. In some embodiments, the human monoclonal anti-bodies of the present invention are administered by slow continuous infusion over a long period, such as more than 24 hours, in order to minimize any unwanted side effects. An effective dose of an antibody of the present invention may also be administered using a weekly, biweekly or triweekly dosing period. The dosing period may be restricted to, e.g., 8 weeks, 12 weeks or until clinical progression has been established. As non-limiting examples, treatment according to the present invention may be provided as a daily dosage of an antibody of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

Typically, the antibody of the present invention is administered to the subject in the form of a pharmaceutical composition which comprises a pharmaceutically acceptable carrier. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. For use in administration to a patient, the composition will be formulated for administration to the patient. The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques. Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added. Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topical application for the lower intestinal tract can be effected in a rectal suppository formulation (see above) or in a suitable enema formulation. Patches may also be used. The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

For example, an antibody present in a pharmaceutical composition of this invention can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of this invention may between about 1 mg/m$^2$ and 500 mg/m$^2$. However, it will be appreciated that these schedules are exemplary and that an optimal schedule and regimen can be adapted taking into account the affinity and tolerability of the particular antibody in the pharmaceutical composition that must be determined in clinical trials. A pharmaceutical composition of the invention for injection (e.g., intramuscular, i.v.) could be prepared to contain sterile buffered water (e.g. 1 ml for intramuscular), and between about 1 ng to about 100 mg, e.g. about 50 ng to about 30 mg or more preferably, about 5 mg to about 25 mg, of an anti-BTN2 antibody of the invention.

The invention will be further illustrated by the following figures and examples. However, these examples and figures should not be interpreted in any way as limiting the scope of the present invention.

LEGENDS OF THE FIGURES

FIG. 1: Binding of BTN2 mAbs on HEK293F cells. HEK293F cells were transfected with BTN2A2-Flag plasmid. At day 1 after transfection, BTN2A2 transfected HEK293F cells (A) and non-transfected HEK293F cells (B) were stained with purified mouse anti-human BTN2 mAbs for 20 min at 4° C. Monoclonal ANTI-FLAG™ antibody serves as positive control for transfection. After 2 washes, cells were incubated with a secondary goat anti-mouse IgG PE for 20 min at 4° C. and a marker for cell viability. Cells were acquired on a LSRFortessa™ (BD) and analyzed with FlowJo™ (TreeStar).

Figure 2:
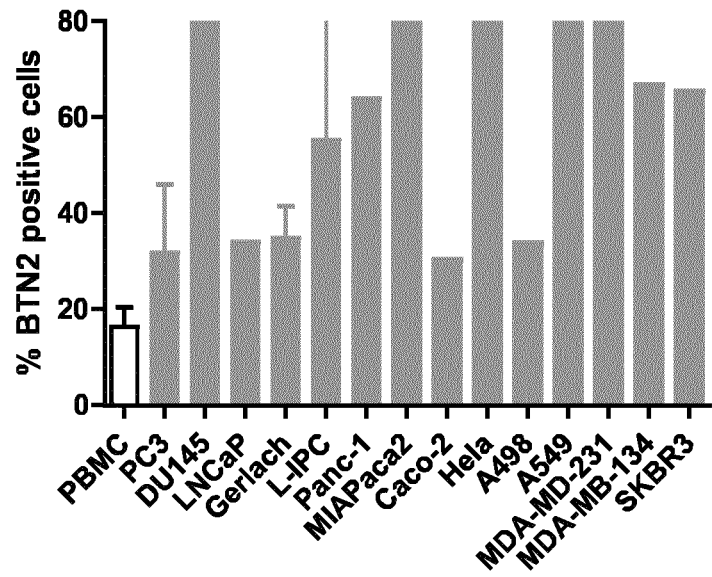
Figure 2:
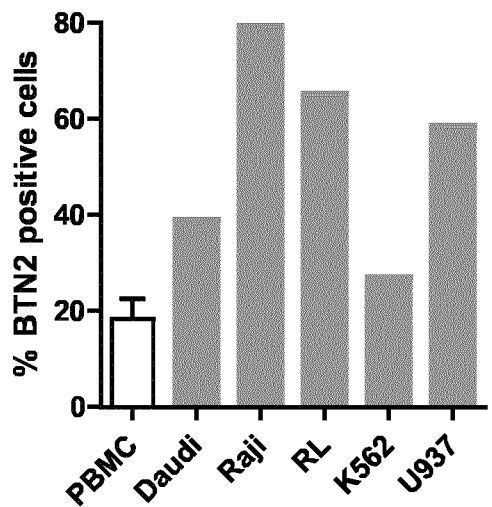

FIG. 2: BTN2 is expressed on cancer cell lines. Cancer cell lines derivated from solid tumors (A), or hematopoietic malignancies (B) were stained with purified BTN2 (8.16) mAb (10 µg/ml) for 20 min at 4° C. After 2 washes, cells were incubated with a secondary goat anti-mouse IgG PE for 20 min at 4° C. and a marker for cell viability. Cells were acquired on a LSRFortessa™ (BD) and analyzed with FlowJo™ (TreeStar). Cell lines were derived from: prostate cancer (PC3, DU145, LNCaP), melanoma (Gerlach), pancreatic cancer (L-IPC, Panc-1, Mia-PACA-2), colorectal cancer (Caco-2), Hela (cervical cancer), renal cancer (A498), lung cancer (A549), breast cancer (MDA-MB-134, MDA-MB-231, SKBR3), Burkitt lymphoma (Daudi, Raji), Non-Hodgkin's lymphoma (RL), chronic myelogenous leukemia (K562), acute myeloid leukemia (U937).

Figure 3:
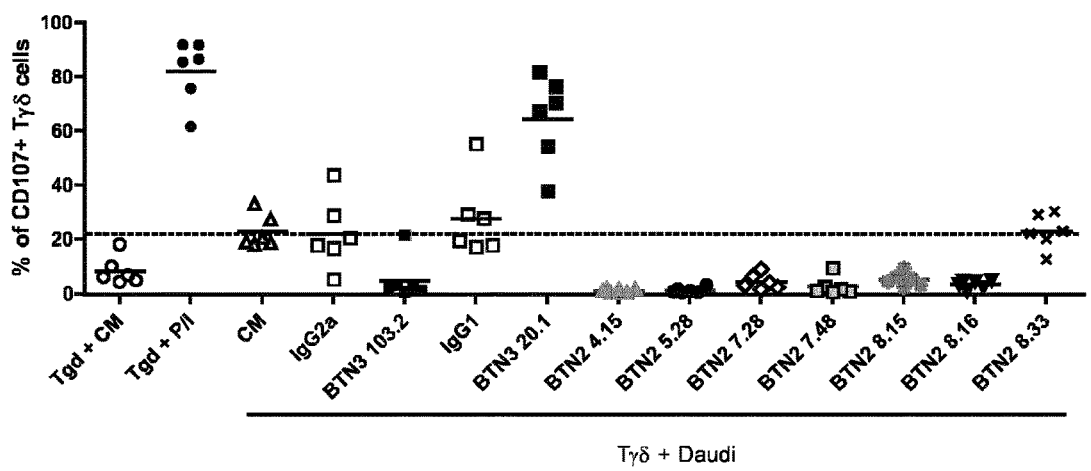
Figure 3:
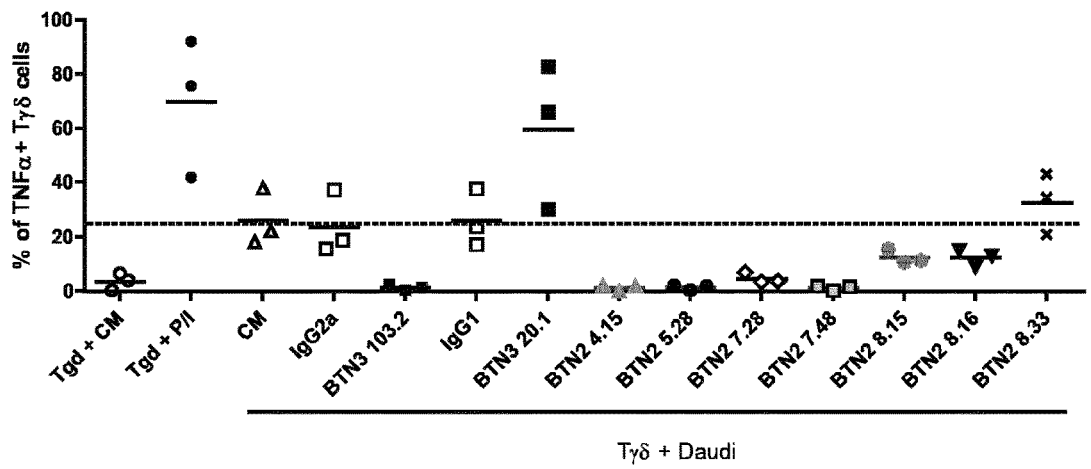
Figure 3:
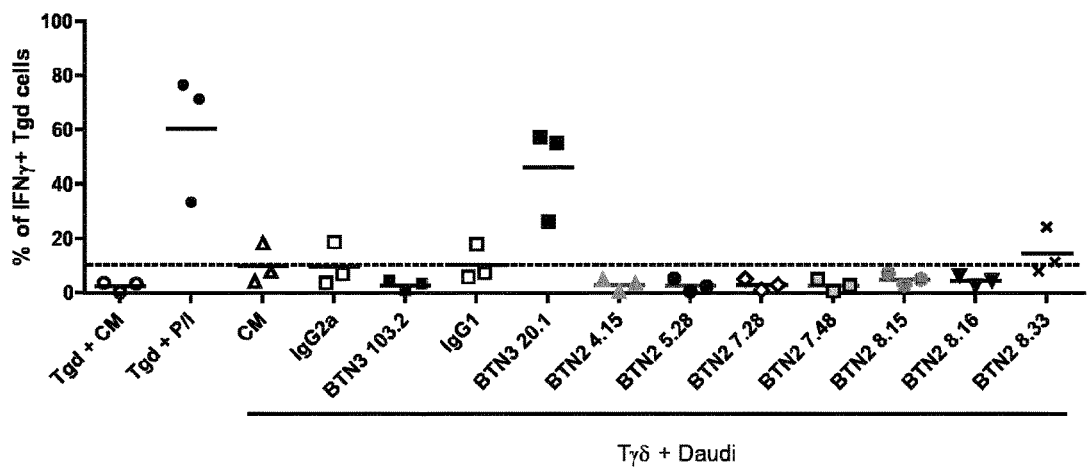

FIG. 3: BTN2 mAbs inhibit the cytolytic function of Vγ9Vδ2 T cells. γδ-T cells were expanded from PBMCs of 6 healthy donors (see Material and Methods). Purified γδ-T cells were simulated overnight in IL-2 (200 UI/ml). Then, γδ-T cells were co-cultured at 37° C. with Daudi target cell line (at effector: target (E:T) ratio of 1:1) with anti-CD107a and anti-CD1072 antibodies and with or without anti-BTN2 (4.15, 5.28, 7.28, 7.48, 8.15, 8.16, 8.33) mAbs (10 µg/ml). After 4 h, cells were collected, fixed and permeabilized, then stained with intracellular mAb (IFN-γ, TNF-α) and analyzed by flow cytometry. The figure shows (A) the degranulation of γδ-T cells, and the production of inflammatory cytokines (B) TNF-α, (C) IFN-γ. Lower dashed line represents the basal cytolytic function of γδ-T cells against Daudi cell line.

Figure 4:
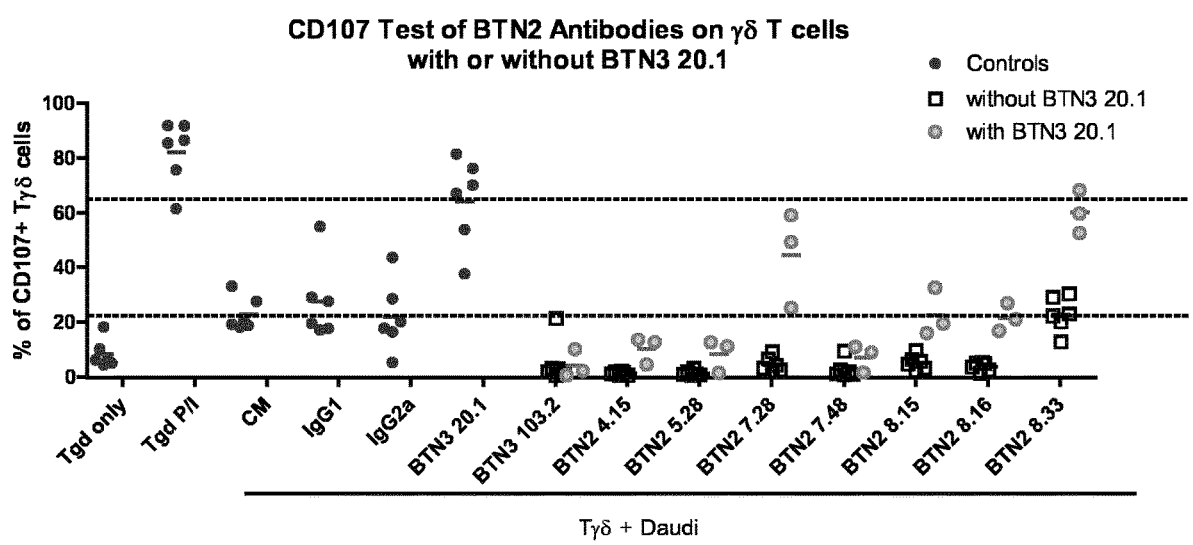

FIG. 4: BTN2 mAbs inhibit the agonist effect of anti-CD277 (20.1) mAb on the cytolytic function of Vγ9Vδ2 T cells. Purified γδ-T cells were simulated overnight in IL-2 (200 UI/ml). Then, γδ-T cells were co-cultured at 37° C. with Daudi target cell line (at effector: target (E:T) ratio of 1:1) with anti-CD107a and anti-CD1072 antibodies and Golgi stop, with or without anti-BTN2 (4.15, 5.28, 7.28, 7.48, 8.15, 8.16, 8.33) mAbs in combination or not with anti-CD277 20.1 mAb. After 4 h, cells were collected and analyzed by flow cytometry. The figure shows the percentage of CD107 (degranulation marker) positive cells among γδ-T cells. Lower dashed line represents the basal degranulation of γδ-T cells against Daudi cell line. Upper dashed line represents the median degranulation observed with anti-CD277 20.1 antibody.

Figure 5:
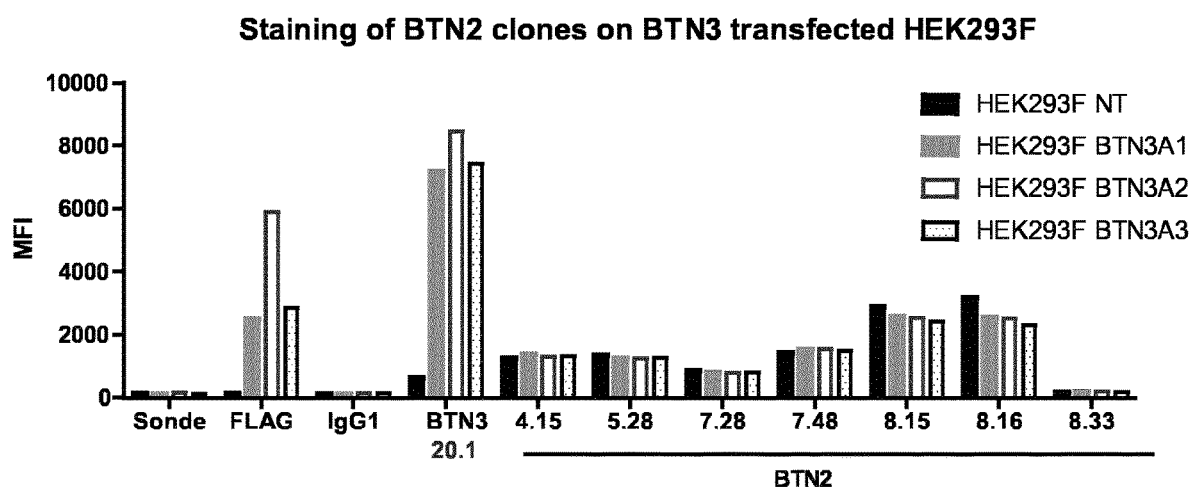

FIG. 5: BTN2 mAbs does not cross-react with HEK293F cells transfected with CD277 isoforms (BTN3A1, BTN3A2 or BTN3A3). HEK293F cells transfected with BTN3A1, BTN3A2, BTN3A3 and non-transfected HEK293F cells were stained with purified mouse anti-human BTN2 mAbs, or with mouse anti-human CD277 20.1 mAb, or with isotypic control IgG1 for 20 min at 4° C. ANTI-FLAG™ serves as positive control for transfection. After 2 washes, cells were incubated with a secondary goat anti-mouse IgG PE for 20 min at 4° C. and a marker for cell viability. Cells were acquired on a LSRFortessa™ (BD) and analyzed with FlowJo™ (TreeStar).

EXAMPLES

Material and Methods
Cell Culture

Peripheral blood mononuclear cells (PBMCs) were obtained from healthy volunteer donors (HV) provided by the local Blood Bank (EFS-Marseille-France) and isolated by density gradient (Eurobio).

The Burkitt lymphoma cell line, Daudi, was obtained from the American Type Culture Collection and cultured (0.5×10$^6$/mL) in RPMI 1640 medium with 10% FCS.
Expansion of γδ-T Cells Effector γδ-T cells were established as previously described. PBMCs from HV were stimulated with Zoledronate (Sigma, 1 µM) and rhIL-2 (Proleukin, 200 IU/mL) at Day 0. From Day 5, rhIL-2 was renewed every two days and cells were kept at 1.15×10$^6$/mL for 15 days. The last day, the purity of γδ T cells was evaluated by flow cytometry. Only cells cultures that reached more than 80% of γδ T Cells, were selected to be used in functional tests. Purified γδ-T cells were thawed until use.
Generation of Monoclonal Antibodies (mAbs)

The mouse anti-human BTN2 antibodies (clones 4.15, 5.28, 7.28, 7.48, 8.15, 8.16, 8.33 with IgG1 isotype) and mouse anti-human CD277 (also known as BTN3A; clone 20.1 with IgG1 isotype) were purified from cell culture supernatants.
Flow Cytometry PBMCs, purified γδ-T cells or tumor cell lines were incubated with specified mAbs before analysis on LSR- Fortessa™ (Becton Dickinson) using DIVA software (BD bioscience). Antibodies used for γδ-T cell degranulation assay were: anti-CD107a-FITC (BD Biosciences), anti-CD107b-FITC (BD Biosciences), anti-CD3-PeVio700 (Miltenyi), anti-Tgd-PE (Miltenyi), live/dead near IR (Thermofisher). Antibodies used for screening of BTN2 expression on tumor cell lines were: purified anti-BTN2 (clone 8.16, 10 µg/ml), FcR Block reagent (Miltenyi), goat anti-mouse-PE (Jackson immunoresearch), live/dead near IR (Thermofisher).

Functional assay on γδ-T cells

Purified γδ-T cells from HV were cultured overnight in IL-2 (200 UI/ml). Then, γδ-T cells were co-cultured at 37° C. with Daudi target cell line (at effector: target (E:T) ratio of 1:1), and cytotoxic tests were performed in 4-hours assays in the presence of GolgiStop™ and soluble CD107 (a&b)-FITC, with or without anti-BTN2 (4.15, 5.28, 7.28, 7.48, 8.15, 8.16, 8.33) mAbs and/or anti-CD277 20.1 mAb (10 µg/ml), with or without activation by phosphoagonists (Pag). After 4 hours, cells were collected, fixed and permeabilized then stained with intracellular mAb (IFN-γ, TNF-α). Cells were finally re-suspended in PBS 2% paraformaldehyde and extemporaneously analyzed on a BD LSR-Fortessa™ (BD Biosciences, San Jose, Calif.). The degree of cytolytic function of γδ-T cells was measured based on the percentage of cells positive for CD107a and CD107b (degranulation) and/or the production of inflammatory cytokines (IFN-γ, TNF-α).

Binding Test of Anti-BTN2 mAbs on for BTN2A1 and BTN2A2 Expressing Cells

HEK-293F cells bearing CRISPR-Cas9-mediated deletions of all isoforms of BTN3 and BTN2 (293F BTN3/BTN2 KO) were generated (data not shown), cultured in DMEM (Life Technologies) 10% fetal bovine serum (FBS, Gibco) 1 mM sodium pyruvate (Thermofisher scientific), and transfected independently with pcDNA3-Zeo-BTN2A1-CFP or pcDNA3-Zeo-BTN2A2-CFP, which encode BTN2A1 and BTN2A2 CFP(Nter)-fusion proteins, using Lipofectamine™ 2000 reagent (Thermofisher scientific) according to manufacturer's instructions.

Flow Cytometry

Twenty-four hours after transfection, cells ($5 \times 10^4$/sample) were collected and stained in duplicate with the indicated concentrations (2-fold dilutions starting from 20 µg/mL to 64 pg/mL) of all 7 purified anti-human BTN2 mAbs in 50 µL of staining buffer (DPBS1X (Thermofisher Scientific) 1% FBS, 1 mM EDTA (Thermofisher Scientific)) during 30 minutes at 4° C. Equal concentrations of mouse IgG1 antibody (Miltenyi) were used as isotype control for staining. Then, cells were washed twice with 200 µL of staining buffer, and incubated with a 1:200 dilution of goat anti-mouse Ig-PE conjugated (Jackson Immunoresearch) in staining buffer for 30 min at 4° C. in the dark. Finally, cells were washed twice in staining buffer prior to fixation using BD Cytofix™ reagent (BD Bioscience) according to manufacturer's instructions. Mean fluorescence intensity (MFI) on PE channel within the CFP-positive population was assessed for each sample in a CytoFLEX LX (Beckman Coulter), and analyzed with a FlowJo™ V10.4.2 software (FlowJo™, LLC 2006-2018).

Statistics $EC_{50}$ of purified anti-human BTN2 mAbs on BTN2A1- and BTN2A2-transfected 293F BTN3/BTN2 KO cells were determined based on log(dose) response curves after non-linear regression following a variable-slope model. These analyses were performed using GraphPad Prism 7.04 software (GraphPad).

Proliferation of γδ-T Cells

γδ-T cells were isolated from PBMCs of healthy donors using anti-TCR γδ microbead kit (Miltenyi Biotec). The purity of γδ-T cells assessed by flow cytometry was greater than 80%. γδ-T cells were labeled with CellTrace™ Violet for 20 minutes at 37° C. Then, $5 \cdot 10^5$ CellTrace™-labeled cells were cultured in 96-well round-bottom plates in the presence of 200 UI/ml IL-2, with or without Pag, and with or without anti-BTN2 antibodies (10 µg/ml). After 5 days of culture, CellTrace™ dilution was evaluated by flow cytometry on a BD LSRFortessa™ (BD Biosciences, San Jose, Calif.).

Statistics

Results are expressed as median±SEM. Statistical analysis was performed using Spearman correlation, Wilcoxon test and Mann-Whitney t test. p values <0.05 were considered significant. Analyses were performed using GraphPad Prism program.

Results

Identification of the Reference Antibodies mAb1-mAb7

The reference antibodies mAb 1-mAb7 were obtained as follows:

Mice were immunized with BTN2A1-Fc antigen. The splenocytes of the mice were collected and fused with myeloma to obtain hybridomas. Hybridomas producing the antibodies with the highest affinity to BTN2 were screened and isolated, yielding the hybridomas as deposited under CNCM I-5231, CNCM I-5232, CNCM I-5233, CNCM I-5234, CNCM I-5235, CNCM I-5236 and CNCM I-5237 capable of producing mAb1-mAb7 respectively.

The hybridoma producing mAb7 (mAb 8.33) which serves as a comparative control for the antibodies according to the present disclosure has been deposited at the Collection Nationale de Cultures des Microorganismes (CNCM, Institut Pasteur, 25 rue du Docteur Roux, 75724 Paris Cedex 15, France) in accordance with the terms of Budapest Treaty on Sep. 14, 2017.

The deposited hybridoma for mAb 8.33 has CNCM deposit number CNCM I-5237.

Binding of mAbs 1-6 on HEK293F Cells.

The graphs in FIG. 1 show a titration curve of the affinity of mouse anti-human BTN2 mAbs on HEK293F cells transfected with human BTN2A2 (FIG. 1A) or non-transfected HEK293F cells (FIG. 1B).

The $EC_{50}$ of each antibody is indicated in the table below. All the antibodies tested were able to recognize and bind to BTN2A2 onto the HEK cells, except mAb 8.33 (mAb7) that does not bind to BTN2A2 by flow cytometry.

| Antibody | Clone Name | $EC_{50}$ (µg/ml) |
|---|---|---|
| mAb1 | mAb 4.15 | 0.07 |
| mAb2 | mAb 5.28 | 0.07 |
| mAb3 | mAb 7.28 | 31.3 |
| mAb4 | mAb 7.48 | 0.08 |
| mAb5 | mAb 8.15 | 0.1 |
| mAb6 | mAb 8.16 | 0.11 |
| mAb7 | mAb 8.33 | — |

BTN2 Polypeptide is Expressed on Cancer Cell Lines.

Tumor cell lines were incubated with mAb6 (mouse anti-human BTN2 mAb 8.16) and then with secondary goat anti-mouse-PE. As shown in Figure A, a wide expression of BTN2 protein on panel of tumor cell lines, derivated from solid tumors or hematopoietic malignancies, was observed, including Daudi cell line (Burkitt lymphoma), a standard cell line used in Vγ9Vδ2 T cell degranulation assay.

mAbs 1-6 Inhibit the Cytolytic Function of Vγ9Vδ2 T Cells.

Purified Vγ9Vδ2 T cells were expanded from PBMCs of healthy donors. Vγ9Vδ2 T cells were co-cultured with Daudi target cells. As shown in FIG. 3, the addition of anti-BTN2 mAbs 1-6 lead to an inhibition of the cytolytic function of Vγ9Vδ2 T cells, as measured as CD107 degranulation, and the production of inflammatory cytokines (TNF-α, IFN-γ) against Daudi target cell line.

Control antibody mAb 7 (mAb 8.33), which does not bind to BTN2A2 by flow cytometry, has no effect on Vγ9Vδ2 T cell degranulation (cytolytic function) or production of inflammatory cytokines.

Anti-CD277 20.1 agonist antibody serves as a control example of an activating antibody of Vγ9Vδ2 T cell degranulation, and anti-CD277 103.2 antagonist antibody serves as a control example of an inhibiting antibody of Vγ9Vδ2 T cell degranulation.

mAbs 1-6 Inhibit the Agonist Effect of Anti-CD277 (20.1) mAb on the Cytolytic Function of Vγ9Vδ2 T Cells.

We also tested the effect of the combination of anti-BTN2 mAbs 1-6 in the presence of the agonist anti-CD277 20.1 mAb, (as disclosed in WO2012/080351) and known to increase the degranulation of Vγ9Vδ2 T cells.

As shown in FIG. 4, mAbs 1, 2 and 4 (respectively anti-BTN2 mAbs 4.15, 5.28, 7.48) surprisingly inhibit the agonist effect of anti-CD277 20.1 antibody on the cytolytic function of Vγ9Vδ2 T cells against Daudi target cell line.

mAbs 5 and 6 (respectively Anti-BTN2 8.15, 8.16) partially inhibit the agonist effect of anti-CD277 20.1 antibody on the cytolytic function of Vγ9Vδ2 T cells against Daudi target cell line.

mAb 3 (anti-BTN2 7.28) and mAb 7 (anti-BTN2 8.33) does not show significant inhibition of the agonist effect of anti-CD277 20.1 antibody on the cytolytic function of Vγ9Vδ2 T cells against Daudi target cell line.

The combination of antagonist 103.2 and agonist 20.1 anti-CD277 serves as a control: antagonist 103.2 antibody inhibits the agonist effect of 20.1 antibody on the cytolytic function of Vγ9Vδ2 T cells against Daudi target cell line, as previously described.

The results of the characterization of mAbs 1-6 (and control mAb 7) are summarized hereafter:

| Clone | $EC_{50}$ (μg/ml) on HEK-BTN2 cells | Effect on γδ T cells/CD107 | Effect on γδ T cells/CD107 in presence of 20.1 |
|---|---|---|---|
| 4.15 | 0.07 | Inhibition | Inhibition |
| 5.28 | 0.07 | Inhibition | Inhibition |
| 7.28 | 31.30 | Inhibition | No effect |
| 7.48 | 0.08 | Inhibition | Inhibition |
| 8.15 | 0.10 | Inhibition | Partial inhibition |
| 8.16 | 0.11 | Inhibition | Partial inhibition |
| 8.33 | — | No | No effect | mAbs 1-6 does not Cross-React with HEK293F Cells Transfected with CD277 Isoforms (BTN3A1, BTN3A2 or BTN3A3).

Binding of BTN2 mAbs on HEK293F cells transfected with any one of the isoforms of CD277 (BTN3A1, BTN3A2 or BTN3A3) is similar as the one observed on non-transfected HEK293F cells (see FIG. 5). We can conclude that anti-BTN2 mAbs does not cross-react with one of the isoform of CD277.

mAbs 1-6 has Binding Specificity with Human BTN2A1 and BTN2A2 Isoforms

Binding of mAbs 1-6 on BTN3/BTN2 KO HEK293F Cells.

EC50 of each antibody on BTN2A1 and BTN2A2 are indicated in the table below. All anti-BTN2 antibodies tested were able to bind both isoforms, excepting mAb 8.33 (mAb7), which does not display staining on flow cytometry.

| Antibody | Clone Name | BTN2A1 $EC_{50}$ (μg/ml) | BTN2A2 $EC_{50}$ (μg/ml) |
|---|---|---|---|
| mAb1 | mAb 4.15 | 0.06 | 0.01 |
| mAb2 | mAb 5.28 | 0.04 | 0.01 |
| mAb3 | mAb 7.28 | 0.02 | 11.8 |
| mAb4 | mAb 7.48 | 0.02 | 0.01 |
| mAb5 | mAb 8.15 | 0.08 | 0.5 |
| mAb6 | mAb 8.16 | 0.08 | 2.4 |
| mAb7 | mAb 8.33 | — | — |

Summary Table:

| Antibody | Clone Name | BTN2A1 $EC_{50}$ (μg/ml) | BTN2A2 $EC_{50}$ (μg/ml) | Tγδ degranulation (% of inhibition) Against target cells (Daudi) | Tγδ degranulation (% of inhibition) Against target cells (Daudi) + anti-BTN3 (20.1) mAb |
|---|---|---|---|---|---|
| mAb1 | mAb 4.15 | 0.06 | 0.01 | >90% | >90% |
| mAb2 | mAb 5.28 | 0.04 | 0.01 | | |
| mAb3 | mAb 7.28 | 0.02 | 11.8 | | ≤10% |
| mAb4 | mAb 7.48 | 0.02 | 0.01 | | >90% |
| mAb5 | mAb 8.15 | 0.08 | 0.5 | | ≤50% |
| mAb6 | mAb 8.16 | 0.08 | 2.4 | | |
| mAb7 | mAb 8.33 | — | — | No effect | No effect |

Nucleotides and Amino Acid Sequences for Practicing the Claimed Invention

| SEQ ID NO: | Brief Description | |
|---|---|---|
| 1 | BTN2A1 aa sequence | MESAAALHFS RPASLLLLLL SLCALVSAQF IVVGPTDPIL ATVGENTTLR CHLSPEKNAE DMEVRWFRSQ FSPAVFVYKG GRERTEEQME EYRGRTTFVS KDISRGSVAL VIHNITAQEN GTYRCYFQEG RSYDEAILHL VVAGLGSKPL ISMRGHEDGG IRLECISRGW YPKPLTVWRD PYGGVAPALK EVSMPDADGL FMVTTAVIIR DKSVRNMSCS INNTLLGQKK ESVIFIPESF MPSVSPCAVA LPIIVVILMI PIAVCIYWIN KLQKEKKILS GEKEFERETR EIALKELEKE |

| SEQ ID NO: | Brief Description | |
|---|---|---|
| | | RVQKEEELQV KEKLQEELRW RRTFLHAVDV VLDPDTAHPD LFLSEDRRSV RRCPFRHLGE SVPDNPERFD SQPCVLGRES FASGKHYWEV EVENVIEWTV GVCRDSVERK GEVLLIPQNG FWTLEMHKGQ YRAVSSPDRI LPLKESLCRV GVFLDYEAGD VSFYNMRDRS HIYTCPRSAF SVPVRPFFRL GCEDSPIFIC PALTGANGVT VPEEGLTLHR VGTHQSL |
| 2 | BTN2A2 aa sequence | MEPAAALHFS LPASLLLLLL LLLLSLCALV SAQFTVVGPA NPILAMVGEN TTLRCHLSPE KNAEDMEVRW FRSQFSPAVF VYKGGRERTE EQMEEYRGRI TFVSKDINRG SVALVIHNVT AQENGIYRCY FQEGRSYDEA ILRLVVAGLG SKPLIEIKAQ EDGSIWLECI SGGWYPEPLT VWRDPYGEVV PALKEVSIAD ADGLFMVTTA VIIRDKYVRN VSCSVNNTLL GQEKETVIFI PESFMPSASP WMVALAVILT ASPWMVSMTV ILAVPIIFMA VSICCIKKLQ REKKILSGEK KVEQEEKEIA QQLQEELRWR RTFLHAADVV LDPDTAHPEL FLSEDRRSVR RGPYRQRVPD NPERFDSQPC VLGWESFASG KHYWEVEVEN VMVWTVGVCR HSVERKGEVL LIPQNGFWTL EMFGNQYRAL SSPERILPLK ESLCRVGVFL DYEAGDVSFY NMRDRSHIYT CPRSAFTVPV RPFFRLGSDD SPIFICPALT GASGVMVPEE GLKLHRVGTH QSL |
| 3 | mAb 4.15 HCDR1 aa | SYDIN |
| 4 | mAb 4.15 HCDR2 aa | WIFPGDDSIIQNEKFKG |
| 5 | mAb 4.15 HCDR3 aa | LGPLRGFTY |
| 6 | mAb 4.15 LCDR1 aa | RASESVDRYGSSFMH |
| 7 | mAb 4.15 LCDR2 aa | RASNLES |
| 8 | mAb 4.15 LCDR3 aa | QQSNEDPWT |
| 9 | mAb 4.15 VH aa | MGWSWVFLFLLSVTAGVHSQVQLQQSGAELVKPGASVKLSCKAS GYIFTSYDINWVRQRPEQGLEWIGWIFPGDDSIIQNEKFKGKAT LITDKSSSTVYMQLSRLTSEDSAVYFCARLGPLRGFTYWGQGTL VTVSA |
| 10 | mAb 4.15 VL aa | METDILLLWVLLLWVPGSTGDIVLIQSPASLAVSLGQRATISCR ASESVDRYGSSFMHWYQQKPGQPPKLLIYRASNLESGIPARFSG SGSRTDFTLTINPVEADDVATYYCQQSNEDPWTFGGGTKLEIK |
| 11 | mAb 5.28 HCDR1 aa | DYSMN |
| 12 | mAb 5.28 HCDR2 aa | RINTETGEPTYADDFKG |
| 13 | mAb 5.28 HCDR3 aa | DYAKR |
| 14 | mAb 5.28 LCDR1 aa | KASQDVITAVA |
| 15 | mAb 5.28 LCDR2 aa | STSYRYT |
| 16 | mAb 5.28 LCDR3 aa | LQHYTTPWT |
| 17 | mAb 5.28 VH aa | MAWVWTLLFLMAAAQSIQAQIQLVQSGPELKKPGETVKISCKAS GYTFTDYSMNWVKQAPGKGLKWVGRINTETGEPTYADDFKGRFA FSLETSASTAYLQIKNLKEDTATYFCVRDYAKRWGQGTSVTVS S |
| 18 | mAb 5.28 VL aa | MGIKMESQIQVFVFVSLWLSGVDGDIVMTQSHKFMSTSVGDRVS ITCKASQDVITAVAWYQQKPGQSPKLLIYSTSYRYTGVPDRFTG SGSGTDFTFTISSVQAEDLAVYYCLQHYTTPWTFGGGTKLEIK |

| SEQ ID NO: | Brief Description | |
|---|---|---|
| 19 | mAb 7.28 HCDR1 aa | SYWIE |
| 20 | mAb 7.28 HCDR2 aa | EILPGSGSTKYNEKFRG |
| 21 | mAb 7.28 HCDR3 aa | LKGYYGGGAMDY |
| 22 | mAb 7.28 LCDR1 aa | RASKSISKYLA |
| 23 | mAb 7.28 LCDR2 aa | SGSTLQS |
| 24 | mAb 7.28 LCDR3 aa | QQHNEYPWT |
| 25 | mAb 7.28 VH aa | MEWTWVFLFLLSVTAGVHSQVHLQQSGAELMKPGASVKISCKAT GYTFSSYWIEWVKQRPGHGREWIGEILPGSGSTKYNEKFRGKAT FAADTSSNTAYVQLSSLTSEDSAVYYCARLKGYYGGGAMDYWGQ GTSVTVSS |
| 26 | mAb 7.28 VL aa | MRFQVQVLGLLLLWISGAQCDVQITQSPSYLAASPGETITINCR ASKSISKYLAWYQEKPGKTNELLIYSGSTLQSGIPSRFSGSGSG TDFTLTISSLEPEDFAMYYCQQHNEYPWTEGGGTKLEIK |
| 27 | mAb 7.48 HCDR1 aa | DEYMY |
| 28 | mAb 7.48 HCDR2 aa | TISDGGSHTYYPDSVKG |
| 29 | mAb 7.48 HCDR3 aa | DTTIITPY |
| 30 | mAb 7.48 LCDR1 aa | RSSTGAVTTSNYAN |
| 31 | mAb 7.48 LCDR2 aa | GTNNRAP |
| 32 | mAb 7.48 LCDR3 aa | GLWYSNHWV |
| 33 | mAb 7.48 VH aa | MNFGLSLIFLVLVLKGVQCEVQLVESGGDLVKPGGSLKLSCAAS GFTFSDFYMYWVRRTPEKRLEWVATISDGGSHTYYPDSVKGRFT ISRDNAKNNLYLQMRSLKSEDTAMYYCGRDTTIITPYWGQGTLV TVSA |
| 34 | mAb 7.48 VL aa | MAWISLILSLLALSSGAISQSVVTQESALTTSPGETVTLTCRSS TGAVTTSNYANWVQEKPDHLFTGLIGGTNNRAPGVPARFSGSLI GDKAALTITGAQTEDEAIYFCGLWYSNHWVFGGGTKLTVL |
| 35 | mAb 8.15 HCDR1 aa | GYWMT |
| 36 | mAb 8.15 HCDR2 aa | EINPDSSTINYTPSLRD |
| 37 | mAb 8.15 HCDR3 aa | GSYYPSY |
| 38 | mAb 8.15 LCDR1 aa | RASKSVSSSGYSYMN |
| 39 | mAb 8.15 LCDR2 aa | LASNLES |
| 40 | mAb 8.15 LCDR3 aa | QHSRELPHT |

-continued

| SEQ ID NO: | Brief Description | |
|---|---|---|
| 41 | mAb 8.15 VH aa | MDFGLIFFIVALLKGVQCEVKLLESGGGLVQPGGSLKLSCAASG FDFSGYWMTWVRQAPGKGLEWIGEINPDSSTINYTPSLRDKFII SRDNAKNTLYLQMSKVRSEDTALYFCARGSYYPSYWGQGTLVTV SA |
| 42 | mAb 8.15 VL aa | METDTLLLWVLLLWVPGSTGDIVLTQSPASLAVSLGQRATISCR ASKSVSSSGYSYMNWYQQKPGQPPKLLIYLASNLESGVPARFSG SGSGTDFTLNIHPVEDEDAATYYCQHSRELPHTFGGGTKLEIK |
| 43 | mAb 8.16 HCDR1 aa | GYWMT |
| 44 | mAb 8.16 HCDR2 aa | EINPDSSTINYTPSLRD |
| 45 | mAb 8.16 HCDR3 aa | GSYYPSY |
| 46 | mAb 8.16 LCDR1 aa | RASKSVSSSGYSYMN |
| 47 | mAb 8.16 LCDR2 aa | LASNLES |
| 48 | mAb 8.16 LCDR3 aa | QHSRELPHT |
| 49 | mAb 8.33 VH aa | MDFGLIFFIVALLKGVQCEVKLLESGGGLVQPGGSLKLSCAASG FDFSGYWMTWVRQAPGKGLEWIGEINPDSSTINYTPSLRDKFII SRDNAKNTLYLQMSKVRSEDTALYFCARGSYYPSYWGQGTLVTV SA |
| 50 | mAb 8.33 VL aa | METDTLLLWVLLLWVPGSTGDIVLTQSPASLAVSLGQRATISCR ASKSVSSSGYSYMNWYQQKPGQPPKLLIYLASNLESGVPARFSG SGSGTDFTLNIHPVEDEDAATYYCQHSRELPHTFGGGTKLEIK |
| 51 | mAb 8.33 HCDR1 aa | SGYYWN |
| 52 | mAb 8.33 HCDR2 aa | YISYDGNNNYNPSLKN |
| 53 | mAb 8.33 HCDR3 aa | PLYDGYYWYFDV |
| 54 | mAb 8.33 LCDR1 aa | ITSTDIDDDMN |
| 55 | mAb 8.33 LCDR2 aa | EANTLRP |
| 56 | mAb 8.33 LCDR3 aa | LQSDNLPYT |
| 57 | mAb 8.33 VH aa | MKVLSLLYLLTAIPGILSDVQLQESGPGLVKPSQSLSLTCSVTG YSITSGYYWNWIRQFPGNKLEWMGYISYDGNNNYNPSLKNRISI TRDTSKNQFFLKLNSVTTEDTATYYCASPLYDGYYWYFDVWGAG TTVTVSS |
| 58 | mAb 8.33 VL aa | MTMFSLALLLSLLLLCVSDSRAETTVTQSPASLSLAIGEKVTIR CITSTDIDDDMNWYQQKPGEPPKLLISEANTLRPGVPSRFSSSG RGTDFVFTIENMLSEDVADYYCLQSDNLPYTFGGGTKLEIK |
| 59 | mAb 4.15 HCDR1 nt | AGCTATGATATAAAC |
| 60 | mAb 4.15 HCDR2 nt | TGGATTTTTCCTGGAGATGATAGTATTATTCAGAATGAGAAGTT CAAGGGC |
| 61 | mAb 4.15 HCDR3 nt | TTGGGCCCATTACGAGGGTTTACTTAC |
| 62 | mAb 4.15 LCDR1 nt | AGAGCCAGTGAAAGTGTTGATCGTTATGGCAGTAGTTTTATGCA C |

-continued

| SEQ ID NO: | Brief Description | |
|---|---|---|
| 63 | mAb 4.15 LCDR2 nt | CGTGCATCCAACCTAGAATCT |
| 64 | mAb 4.15 LCDR3 nt | CAGCAAAGTAATGAGGATCCGTGGACG |
| 65 | mAb 4.15 VH nt | ATGGGATGGAGCTGGGTCTTTCTCTTCCTCCTGTCAGTAACTGC AGGTGTCCACTCCCAGGTTCAGCTGCAGCAGTCTGGAGCTGAAC TGGTAAAGCCTGGGGCTTCAGTGAAGTTGTCCTGCAAGGCTTCT GGCTACATCTTCACAAGCTATGATATAAACTGGGTGAGGCAGAG GCCTGAACAGGGACTTGAGTGGATTGGATGGATTTTTCCTGGAG ATGATAGTATTATTCAGAATGAGAAGTTCAAGGGCAAGGCCACA CTGACTACAGACAAATCCTCCAGCACAGTCTACATGCAGCTCAG CAGGCTGACATCTGAGGACTCTGCTGTCTATTTCTGTGCAAGAT GGGCCCATTACGAGGGTTTACTTACTGGGGCCAAGGGACTCTG GTCACTGTCTCTGCAGGGTTTACTTACTGGGGCCAAGGGACTCT GGTCACTGTCTCTGCA |
| 66 | mAb 4.15 VL nt | ATGGAGACAGACACACTCCTGCTATGGGTGCTGCTGCTCTGGGT TCCAGGTTCCACAGGTGACATTGTGCTGACCCAATCTCCAGCTT CTTTGGCTGTGTCTCTAGGGCAGAGGGCCACCATATCCTGCAGA GCCAGTGAAAGTGTTGATCGTTATGGCAGTAGTTTTATGCACTG GTACCAGCAGAAACCAGGACAGCCACCCAAACTCCTCATCTATC GTGCATCCAACCTAGAATCTGGGATCCCTGCCAGGTTCAGTGGC AGTGGGTCTAGGACAGACTTCACCCTCACCATTAATCCTGTGGA GGCTGATGATGTTGCAACCTATTACTGTCAGCAAAGTAATGAGG ATCCGTGGACGTTCGGTGGAGGCACCAAGCTGGAAATCAAA |
| 67 | mAb 5.28 HCDR1 nt | GACTATTCAATGAAC |
| 68 | mAb 5.28 HCDR2 nt | AGGATCAACACTGAGACTGGTGAGCCAACATATGCAGATGACTT CAAGGGA |
| 69 | mAb 5.28 HCDR3 nt | GACTACGCTAAGCGG |
| 70 | mAb 5.28 LCDR1 nt | AAGGCCAGTCAGGATGTGATTACTGCTGTAGCC |
| 71 | mAb 5.28 LCDR2 nt | TCGACATCCTACCGGTACACT |
| 72 | mAb 5.28 LCDR3 nt | CTGCAACATTATACTACTCCGTGGACG |
| 73 | mAb 5.28 VH nt | ATGGCTTGGGTGTGGACCTTGCTATTCCTGATGGCAGCTGCCCA AAGTATCCAAGCACAGATCCAGTTGGTACAGTCTGGACCTGAGC TGAAGAAGCCTGGAGAGACAGTCAAGATCTCCTGCAAGGCTTCT GGTTATACCTTCACAGACTATTCAATGAACTGGGTGAAACAGGC TCCAGGAAAGGGTTTAAAGTGGGTGGGCAGGATCAACACTGAGA CTGGTGAGCCAACATATGCAGATGACTTCAAGGGACGGTTTGCC TTCTCTTTGGAAACCTCTGCCAGCACTGCCTATTTGCAGATCAA AAACCTCAAAAATGAGGACACGGCTACATATTTCTGTGTTAGAG ACTACGCTAAGCGGTGGGGTCAAGGAACCTCAGTCACCGTCTCC TCA |
| 74 | mAb 5.28 VL nt | ATGGGCATCAAAATGGAGTCACAGATTCAGGTCTTTGTATTCGT GTCTCTCTGGTTGTCTGGTGTTGACGGAGACATTGTGATGACCC AGTCTCACAAATTCATGTCCACATCAGTAGGAGACAGGGTCAGC ATCACCTGCAAGGCCAGTCAGGATGTGATTACTGCTGTAGCCTG GTATCAACAGAAACCAGGACAATCTCCTAAACTACTGATTTACT CGACATCCTACCGGTACACTGGAGTCCCTGATCGCTTCACTGGC AGTGGATCTGGGACGGATTTCACTTTCACCATCAGCAGTGTGCA GGCTGAAGACCTGGCAGTTTATTACTGTCTGCAACATTATACTA CTCCGTGGACGTTCGGTGGAGGCACCAAGCTGGAAATCAAA |
| 75 | mAb 7.28 HCDR1 nt | AGCTACTGGATAGAG |
| 76 | mAb 7.28 HCDR2 nt | GAGATTTTACCTGGAAGTGGAAGTACTAAGTACAATGAGAAGTT TAGGGGC |

| SEQ ID NO: | Brief Description | |
|---|---|---|
| 77 | mAb 7.28 HCDR3 nt | TTGAAGGGTTACTACGGAGGAGGTGCTATGGACTAC |
| 78 | mAb 7.28 LCDR1 nt | AGGGCAAGTAAGAGCATTAGCAAATATTTAGCC |
| 79 | mAb 7.28 LCDR2 nt | TCTGGATCCACTTTGCAATCT |
| 80 | mAb 7.28 LCDR3 nt | CAACAGCATAATGAATACCCGTGGACG |
| 81 | mAb 7.28 VH nt | ATGGAATGGACCTGGGTCTTTCTCTTCCTCCTGTCAGTAACTGC AGGTGTCCACTCCCAGGTTCACCTGCAGCAGTCTGGAGCTGAGC TGATGAAGCCTGGGGCCTCAGTGAAAATATCCTGCAAGGCTACT GGCTACACATTCAGTAGCTACTGGATAGAGTGGGTAAAGCAGAG GCCTGGACATGGCCGTGAGTGGATTGGAGAGATTTTACCTGGAA GTGGAAGTACTAAGTACAATGAGAAGTTTAGGGGCAAGGCCACA TTCGCTGCAGATACATCCTCCAACACAGCCTACGTGCAACTCAG CAGCCTGACATCTGAGGACTCTGCCGTCTATTACTGTGCAAGAT TGAAGGGTTACTACGGAGGAGGTGCTATGGACTACTGGGGTCAA GGAACCTCAGTTACCGTCTCTTCA |
| 82 | mAb 7.28 VL nt | ATGAGGTTCCAGGTTCAGGTTCTGGGGCTCCTTCTGCTCTGGAT ATCAGGTGCCCAGTGTGATGTCCAGATAACCCAGTCTCCATCTT ATCTTGCTGCATCTCCTGGAGAAACCATTACTATTAATTGCAGG GCAAGTAAGAGCATTAGCAAATATTTAGCCTGGTATCAAGAGAA ACCTGGGAAAACTAATGAGCTTCTTATCTACTCTGGATCCACTT TGCAATCTGGAATTCCATCAAGGTTCAGTGGCAGTGGATCTGGT ACAGATTTCACTCTCACCATCAGTAGCCTGGAGCCTGAAGATTT TGCAATGTATTACTGTCAACAGCATAATGAATACCCGTGGACGT TCGGTGGAGGCACCAAGCTGGAAATCAAA |
| 83 | mAb 7.48 HCDR1 nt | GACTTTTACATGTAT |
| 84 | mAb 7.48 HCDR2 nt | ACCATTAGTGATGGTGGTAGTCACACCTACTATCCAGACAGTGT GAAGGGG |
| 85 | mAb 7.48 HCDR3 nt | GATACTACGATAATTACTCCTTAC |
| 86 | mAb 7.48 LCDR1 nt | CGCTCAAGTACTGGGGCTGTTACAACTAGTAACTATGCCAAC |
| 87 | mAb 7.48 LCDR2 nt | GGTACCAACAACCGAGCTCCA |
| 88 | mAb 7.48 LCDR3 nt | GGTCTTTGGTACAGCAACCATTGGGTG |
| 89 | mAb 7.48 VH nt | ATGAACTTCGGGCTCAGCTTGATTTTCCTTGTCCTTGTTTTAAA AGGTGTCCAGTGTGAAGTGCAGCTGGTGGAGTCTGGGGGAGACT TAGTGAAGCCTGGAGGGTCCCTGAAACTCTCCTGTGCAGCCTCT GGATTCACTTTCAGTGACTTTTACATGTATTGGGTTCGCCGGAC TCCGGAAAAGAGGCTGGAGTGGGTCGCAACCATTAGTGATGGTG GTAGTCACACCTACTATCCAGACAGTGTGAAGGGGCGATTCACC ATCTCCAGAGACAATGCCAAGAACAACCTCTACCTACAAATGAG AAGTCTGAAGTCTGAGGACACAGCCATGTATTACTGTGGAAGAG ATACTACGATAATTACTCCTTACTGGGGCCAAGGGACTCTGGTC ACTGTCTCTGCA |
| 90 | mAb 7.48 VL nt | ATGGCCTGGATTTCACTTATACTCTCTCCTGGCTCTCAGCTC AGGGGCCATTTCCCAGTCTGTTGTGACTCAGGAATCTGCACTCA CCACATCACCTGGTGAAACAGTCACACTCACTTGTCGCTCAAGT ACTGGGGCTGTTACAACTAGTAACTATGCCAACTGGGTCCAAGA AAAACCAGATCATTTATTCACTGGTCTAATAGGTGGTACCAACA ACCGAGCTCCAGGTGTTCCTGCCAGATTCTCAGGCTCCCTGATT GGGAGACAAGGCTGCCCTCACCATCACAGGGGCACAGACTGAGGA TGAGGCAATATATTTCTGTGGTCTTTGGTACAGCAACCATTGGG TGTTCGGTGGAGGAACCAAACTGACTGTCCTA |
| 91 | mAb 8.15 HCDR1 nt | GGATACTGGATGACT |

-continued

| SEQ ID NO: | Brief Description | |
|---|---|---|
| 92 | mAb 8.15 HCDR2 nt | GAAATTAATCCAGATAGCAGTACGATAAACTATACGCCATCTCT AAGGGAT |
| 93 | mAb 8.15 HCDR3 nt | GGGAGCTACTATCCCTCTTAC |
| 94 | mAb 8.15 LCDR1 nt | AGGGCCAGCAAAAGTGTCAGTTCATCTGGCTATAGTTATATGAA C |
| 95 | mAb 8.15 LCDR2 nt | CTTGCATCCAACCTAGAATCT |
| 96 | mAb 8.15 LCDR3 nt | CAGCACAGTAGGGAGCTTCCGCACACG |
| 97 | mAb 8.15 VH nt | ATGGATTTTGGGCTGATTTTTTTATTGTTGCTCTTTTAAAAGG GGTCCAGTGTGAAGTGAAGCTTCTCGAGTCTGGAGGTGGCCTGG TGCAGCCTGGAGGATCCCTGAAACTCTCCTGTGCAGCCTCAGGA TTCGATTTTAGTGGATACTGGATGACTTGGGTCCGGCAGGCTCC AGGGAAAGGGCTAGAATGGATTGGAGAAATTAATCCAGATAGCA GTACGATAAACTATACGCCATCTCTAAGGGATAAATTCATCATC TCCAGAGACAACGCCAAGAATACGCTGTACCTGCAAATGAGCAA AGTGAGATCTGAGGACACAGCCCTTTATTTCTGTGCAAGAGGGA GCTACTATCCCTCTTACTGGGGCCAAGGGACTCTGGTCACTGTC TCTGCA |
| 98 | mAb 8.15 VL nt | ATGGAGACAGACACACTCCTGTTATGGGTACTGCTGCTCTGGGT TCCAGGTTCCACTGGGGACATTGTGCTGACACAGTCTCCTGCTT CCTTAGCTGTATCTCTGGGGCAGAGGGCCACCATCTCATGCAGG GCCAGCAAAAGTGTCAGTTCATCTGGCTATAGTTATATGAACTG GTACCAGCAGAAACCAGGACAGCCACCCAAACTCCTCATCTATC TTGCATCCAACCTAGAATCTGGGGTCCCTGCCAGGTTCAGTGGC AGTGGGTCTGGGACAGACTTCACCCTCAACATCCATCCTGTGGA GGATGAGGATGCTGCAACCTATTACTGTCAGCACAGTAGGGAGC TTCCGCACACGTTCGGAGGGGGGACCAAGCTGGAAATAAAA |
| 99 | mAb 8.16 HCDR1 nt | GGATACTGGATGACT |
| 100 | mAb 8.16 HCDR2 nt | GAAATTAATCCAGATAGCAGTACGATAAACTATACGCCATCTCT AAGGGAT |
| 101 | mAb 8.16 HCDR3 nt | GGGAGCTACTATCCCTCTTAC |
| 102 | mAb 8.16 LCDR1 nt | AGGGCCAGCAAAAGTGTCAGTTCATCTGGCTATAGTTATATGAA C |
| 103 | mAb 8.16 LCDR2 nt | CTTGCATCCAACCTAGAATCT |
| 104 | mAb 8.16 LCDR3 nt | CAGCACAGTAGGGAGCTTCCGCACACG |
| 105 | mAb 8.33 VH nt | ATGGATTTTGGGCTGATTTTTTTATTGTTGCTCTTTTAAAAGG GGTCCAGTGTGAAGTGAAGCTTCTCGAGTCTGGAGGTGGCCTGG TGCAGCCTGGAGGATCCCTGAAACTCTCCTGTGCAGCCTCAGGA TTCGATTTTAGTGGATACTGGATGACTTGGGTCCGGCAGGCTCC AGGGAAAGGGCTAGAATGGATTGGAGAAATTAATCCAGATAGCA GTACGATAAACTATACGCCATCTCTAAGGGATAAATTCATCATC TCCAGAGACAACGCCAAGAATACGCTGTACCTGCAAATGAGCAA AGTGAGATCTGAGGACACAGCCCTTTATTTCTGTGCAAGAGGGA GCTACTATCCCTCTTACTGGGGCCAAGGGACTCTGGTCACTGTC TCTGCA |
| 106 | mAb 8.33 VL nt | ATGGAGACAGACACACTCCTGTTATGGGTACTGCTGCTCTGGGT TCCAGGTTCCACTGGGGACATTGTGCTGACACAGTCTCCTGCTT CCTTAGCTGTATCTCTGGGGCAGAGGGCCACCATCTCATGCAGG GCCAGCAAAAGTGTCAGTTCATCTGGCTATAGTTATATGAACTG GTACCAGCAGAAACCAGGACAGCCACCCAAACTCCTCATCTATC TTGCATCCAACCTAGAATCTGGGGTCCCTGCCAGGTTCAGTGGC AGTGGGTCTGGGACAGACTTCACCCTCAACATCCATCCTGTGGA GGATGAGGATGCTGCAACCTATTACTGTCAGCACAGTAGGGAGC TTCCGCACACGTTCGGAGGGGGGACCAAGCTGGAAATAAAA |

-continued

| SEQ ID NO: | Brief Description | |
|---|---|---|
| 107 | mAb 8.33 HCDR1 nt | AGTGGTTATTACTGGAAC |
| 108 | mAb 8.33 HCDR2 nt | TACATAAGCTACGACGGTAACAATAACTACAACCCATCTCTCAA AAAT |
| 109 | mAb 8.33 HCDR3 nt | CCTCTCTATGATGGTTATTACTGGTACTTCGATGTC |
| 110 | mAb 8.33 LCDR1 nt | ATAACCAGCACTGATATTGATGATGATATGAAC |
| 111 | mAb 833 LCDR2 nt | GAAGCCAATACTCTTCGTCCT |
| 112 | mAb 8.33 LCDR3 nt | TTGCAAAGTGATAACTTGCCGTACACG |
| 113 | mAb 8.33 VH nt | ATGAAAGTGTTGAGTCTGTTGTACCTGTTGACAGCCATTCCTGG TATCCTGTCTGATGTACAGCTTCAGGAGTCAGGACCTGGCCTCG TGAAACCTTCTCAGTCTCTGTCTCTCACCTGCTCTGTCACTGGC TACTCCATCACCAGTGGTTATTACTGGAACTGGATCCGGCAGTT TCCAGGAAACAAACTGGAATGGATGGGCTACATAAGCTACGACG GTAACAATAACTACAACCCATCTCTCAAAAATCGAATCTCCATC ACTCGTGACACGTCTAAGAACCAGTTTTTCCTGAAGTTGAATTC TGTGACTACTGAGGACACAGCTACATATTACTGTGCAAGTCCTC TCTATGATGGTTATTACTGGTACTTCGATGTCTGGGGCGCAGGG ACCACGGTCACCGTCTCCTCA |
| 114 | mAb 8.33 VL nt | ATGACCATGTTCTCACTAGCTCTTCTCCTCAGTCTTCTTCTCCT CTGTGTCTCTGATTCTAGGGCAGAAACAACTGTGACCCAGTCTC CAGCATCCCTGTCCCTGGCTATAGGAGAAAAAGTCACCATCAGA TGCATAACCAGCACTGATATTGATGATGATATGAACTGGTACCA GCAGAAGCCAGGGGAACCTCCTAAGCTCCTTATTTCAGAAGCCA ATACTCTTCGTCCTGGAGTCCCATCCCGATTCTCCAGCAGTGGC CGTGGTACAGATTTTGTTTTTACAATTGAAAACATGCTCTCAGA AGATGTTGCAGATTACTACTGTTTGCAAAGTGATAACTTGCCGT ACACGTTCGGAGGGGGGACCAAGCTGGAAATAAAA |

REFERENCES

Throughout this application, various references describe the state of the art to which this invention pertains. The disclosures of these references are hereby incorporated by reference into the present disclosure.

---

The invention claimed is:

1. A method of treating an autoimmune or inflammatory disorder or transplant rejection in a subject in need thereof, comprising administering to the subject a therapeutically effective amount of an anti-BTN2 antibody, wherein the anti-BTN2 antibody comprises
   a. the H-CDR1, H-CDR2, HCDR3, L-CDR1, L-CDR2 and L-CDR3 of the mAb 4.15 of SEQ ID NOs:3-8 respectively;
   b. the H-CDR1, H-CDR2, HCDR3, L-CDR1, L-CDR2 and L-CDR3 of the mAb 5.28 of SEQ ID NOs:11-16 respectively;
   c. the H-CDR1, H-CDR2, HCDR3, L-CDR1, L-CDR2 and L-CDR3 of the mAb 7.28 of SEQ ID NOs:19-24 respectively;
   d. the H-CDR1, H-CDR2, HCDR3, L-CDR1, L-CDR2 and L-CDR3 of the mAb 7.48 of SEQ ID NOs:27-32 respectively;
   e. the H-CDR1, H-CDR2, HCDR3, L-CDR1, L-CDR2 and L-CDR3 of the mAb 8.15 of SEQ ID NOs:35-40 respectively; or
   f. the H-CDR1, H-CDR2, HCDR3, L-CDR1, L-CDR2 and L-CDR3 of the mAb 8.16 of SEQ ID NOs:43-48 respectively.

2. The method of claim 1, wherein the anti-BTN2 antibody comprises
   a. a heavy chain wherein the VH region has the sequence SEQ ID NO:9 and a light chain wherein the VL region has the sequence SEQ ID NO:10;
   b. a heavy chain wherein the VH region has the sequence SEQ ID NO:17 and a light chain wherein the VL region has the sequence SEQ ID NO:18;
   c. a heavy chain wherein the VH region has the sequence SEQ ID NO:25 and a light chain wherein the VL region has the sequence SEQ ID NO:26;
   d. a heavy chain wherein the VH region has the sequence SEQ ID NO:33 and a light chain wherein the VL region has the sequence SEQ ID NO:34;
   e. a heavy chain wherein the VH region has the sequence SEQ ID NO:41 and a light chain wherein the VL region has the sequence SEQ ID NO:42; or
   f. a heavy chain wherein the VH region has the sequence SEQ ID NO:49 and a light chain wherein the VL region has the sequence SEQ ID NO:50.

3. The method of claim 1, wherein the autoimmune or inflammatory disorder is selected from the group consisting of: rheumatoid arthritis (RA), insulin-dependent diabetes mellitus (Type 1 diabetes), multiple sclerosis (MS), Crohn's disease, systemic lupus erythematosus (SLE), scleroderma, Sjogren's syndrome, pemphigus vulgaris, pemphigoid, Addison's disease, ankylosing spondylitis, aplastic anemia, autoimmune hemolytic anemia, autoimmune hepatitis, coeliac disease, dermatomyositis, Goodpasture's syndrome, Graves' disease, Guillain-Barre syndrome, Hashimoto's disease, idiopathic leucopenia, idiopathic thrombocytopenic purpura, male infertility, mixed connective tissue disease, myasthenia gravis, pernicious anemia, phacogenic uveitis, primary biliary cirrhosis, primary myxoedema, Reiter's syndrome, stiff man syndrome, thyrotoxicosis, ulcerative colitis, and Wegener's granulomatosis.

4. The method of claim 1, wherein the anti-BTN2 antibody has specificity for both human butyrophilin-2A1 (BTN2A1) and human butyrophilin-2A2 (BTN2A2).

5. The method of claim 1, wherein the anti-BTN2 antibody does not cross-react with human CD277.

6. The method of claim 1, wherein the anti-BTN2 antibody is a human, chimeric or humanized antibody.

* * * * *